US009173882B2

(12) United States Patent
Singh et al.

(10) Patent No.: US 9,173,882 B2
(45) Date of Patent: *Nov. 3, 2015

(54) POLYCYCLIC HETEROARYL SUBSTITUTED TRIAZOLES USEFUL AS AXL INHIBITORS

(71) Applicant: Rigel Pharmaceuticals, Inc., South San Francisco, CA (US)

(72) Inventors: Rajinder Singh, Belmont, CA (US); Thilo J. Heckrodt, San Francisco, CA (US); Sacha Holland, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/688,843

(22) Filed: Apr. 16, 2015

(65) Prior Publication Data

US 2015/0216864 A1 Aug. 6, 2015

Related U.S. Application Data

(63) Continuation of application No. 13/725,407, filed on Dec. 21, 2012, which is a continuation of application No. 13/002,487, filed as application No. PCT/US2009/049617 on Jul. 2, 2009, now Pat. No. 8,349,838.

(60) Provisional application No. 61/079,403, filed on Jul. 9, 2008.

(51) Int. Cl.
*A61K 31/502* (2006.01)

(52) U.S. Cl.
CPC .................................. *A61K 31/502* (2013.01)

(58) Field of Classification Search
CPC ....................................................... A61K 31/502
USPC .......................................... 514/250; 544/234
See application file for complete search history.

(56) References Cited

U.S. PATENT DOCUMENTS

| 3,813,400 | A | 5/1974 | Boyle et al. |
|---|---|---|---|
| 6,924,302 | B2 | 8/2005 | Lin et al. |
| 7,709,482 | B2 | 5/2010 | Goff et al. |
| 7,872,000 | B2 | 1/2011 | Goff et al. |
| 7,879,856 | B2 | 2/2011 | Goff et al. |
| 7,884,119 | B2 | 2/2011 | Singh et al. |
| 7,935,693 | B2 | 5/2011 | Singh et al. |
| 8,012,965 | B2 | 9/2011 | Goff et al. |
| 8,097,630 | B2 | 1/2012 | Singh et al. |
| 8,168,636 | B2 | 5/2012 | Goff et al. |
| 8,288,382 | B2 | 10/2012 | Goff et al. |
| 8,309,566 | B2 | 11/2012 | Bhamidipati et al. |
| 8,349,838 | B2 | 1/2013 | Singh et al. |
| 8,389,557 | B2 | 3/2013 | Singh et al. |
| 8,431,594 | B2 | 4/2013 | Singh et al. |
| 8,492,373 | B2 | 7/2013 | Goff et al. |
| 8,546,433 | B2 | 10/2013 | Hitoshi et al. |
| 8,563,559 | B2 | 10/2013 | Singh et al. |
| 8,609,650 | B2 | 12/2013 | Goff et al. |
| 8,618,331 | B2 | 12/2013 | Goff et al. |
| 8,658,669 | B2 | 2/2014 | Singh et al. |
| 8,735,418 | B2 | 5/2014 | Bhamidipati et al. |
| 8,741,898 | B2 | 6/2014 | Goff et al. |
| 8,796,259 | B2 | 8/2014 | Ding et al. |
| 8,809,347 | B2 | 8/2014 | Goff et al. |
| 8,809,364 | B2 | 8/2014 | Singh et al. |
| 8,906,922 | B2 | 12/2014 | Goff et al. |
| 8,933,080 | B2 | 1/2015 | Singh et al. |
| 2004/0077699 | A1 | 4/2004 | Lin et al. |
| 2004/0214817 | A1 | 10/2004 | Pierce et al. |
| 2005/0118604 | A1 | 6/2005 | Lorens et al. |
| 2006/0293256 | A1 | 12/2006 | Yamada et al. |
| 2008/0182862 | A1 | 7/2008 | Ding et al. |
| 2013/0109695 | A1 | 5/2013 | Singh et al. |
| 2013/0338161 | A1 | 12/2013 | Hitoshi et al. |
| 2014/0155386 | A1 | 6/2014 | Goff et al. |
| 2014/0213585 | A1 | 7/2014 | Bhamidipati et al. |
| 2014/0323490 | A1 | 10/2014 | Goff et al. |
| 2015/0072959 | A1 | 3/2015 | Goff et al. |
| 2015/0126514 | A1 | 5/2015 | Singh et al. |

FOREIGN PATENT DOCUMENTS

| EP | 0 710 654 A1 | 5/1996 |
|---|---|---|
| WO | WO 01/09106 A1 | 2/2001 |
| WO | WO 02/057240 A1 | 7/2002 |
| WO | WO 03/027275 A1 | 4/2003 |
| WO | WO 03/093344 A1 | 11/2003 |
| WO | WO 2004/017997 A1 | 3/2004 |

(Continued)

OTHER PUBLICATIONS

Agrafiotis et al., "SAR Maps: A New SAR Visualization Technique for Medicinal Chemists," *J. Med. Chem.* 50(24): 5926-5937, 2007.

Alexander et al., "Human Parathyroid Hormone 1-34 Reverses Bone Loss in Ovariectomized Mice," *Journal of Bone and Mineral Research* 16(9): 1665-1673, 2001.

Angelillo-Scherrer et al., "Role of Gas6 receptors in platelet signaling during thrombus stabilization and implications for antithrombotic therapy," *Journal of Clinical Investigation* 115(2): 237-246, Feb. 2005.

Bora et al., "Immunotherapy for choroidal neovascularization in a laser-induced mouse model simulating exudative (wet) macular degeneration," *Proc. Natl. Acad. Sci U.S.A.* 100(5): 2679-2684, Mar. 4, 2003.

(Continued)

*Primary Examiner* — Paul V Ward
(74) *Attorney, Agent, or Firm* — Seed IP Law Group PLLC; Travis Young

(57) ABSTRACT

Polycyclic heteroaryl substituted triazoles and pharmaceutical compositions containing the compounds are disclosed as being useful in inhibiting the activity of the receptor protein tyrosine kinase Axl. Methods of using the compounds in treating diseases or conditions associated with Axl activity are also disclosed.

10 Claims, No Drawings

(56) References Cited

FOREIGN PATENT DOCUMENTS

| WO | WO 2004/039955 A2 | 5/2004 |
|---|---|---|
| WO | WO 2004/046120 A2 | 6/2004 |
| WO | WO 2005/013982 A1 | 2/2005 |
| WO | WO 2005/077922 A2 | 8/2005 |
| WO | WO 2007/030680 A2 | 3/2007 |
| WO | WO 2008/083353 A1 | 7/2008 |
| WO | WO 2008/083354 A1 | 7/2008 |
| WO | WO 2008/083356 A1 | 7/2008 |
| WO | WO 2008/083357 A1 | 7/2008 |
| WO | WO 2008/083367 A2 | 7/2008 |
| WO | WO 2008/157131 A1 | 12/2008 |
| WO | WO 2009/054864 A1 | 4/2009 |
| WO | WO 2010/005876 A2 | 1/2010 |
| WO | WO 2010/005879 A1 | 1/2010 |

OTHER PUBLICATIONS

Brewster et al., "Ro 32-3555, an orally active collagenase selective inhibitor, prevents structural damage in the STR/ORT mouse model of osteoarthritis," *Arthritis & Rheumatism* 41(9): 1639-1644, Sep. 1998.
Chung et al., "Expression of the proto-oncogene Axl in renal cell carcinoma," *DNA Cell Biol.* 22(8): 533-540, Aug. 2003 (abstract only).
Daouti et al., "Development of comprehensive functional genomic screens to identify novel mediators of osteoarthritis," *Osteoarthritis Cartilage* 13(6): 508-518, Jun. 2005 (abstract only).
Fujioka et al., "Equol, a Metabolite of Daidzein, Inhibits Bone Loss in Ovariectomized Mice," *Journal of Nutrition* 134: 2623-2627, 2004.
Goswami et al., "Spectrum and Range of Oxidative Stress Responses of Human Lens Epithelial Cells to $H_2O_2$ Insult," *Invest Ophthalmol Vis Sci.* 44(5): 2084-2093, May 2003.
Hafizi et al., "Signalling and functional diversity within the Axl subfamily of receptor tyrosine kinases," *Cytokine Growth Factor Rev.* 17(4): 295-304, Aug. 2006 (abstract only).
Holland et al., "Multiple Roles for the Receptor Tyrosine Kinase Axl in Tumor Formation," *Cancer Res.* 65(20): 9294-9303, Oct. 15, 2005.
Holland et al., "Requirement for the Receptor Tyrosine Kinase Axl in Angiogenesis and Tumor Growth", 7th Annual Symposium on Anti-Angiogenic Agents, Feb. 10-13, 2005, San Diego, California, 1 page.
Holland et al., "R428, a Selective Small Molecule Inhibitor of Axl Kinase, Blocks Tumor Spread and Prolongs Survival in Models of Metastatic Breast Cancer," *Cancer Res* 70(4): 1544-1554, Feb. 15, 2010.
Kadoya et al., "Role of calpain in hydrogen peroxide induced cataract," *Current Eye Research* 12(4): 341-346, 1993.
Katritzky et al., "Syntheses of 5-(2-arylazenyl)-1,2,4-triazoles and 2-amino-5-aryl-1,3,4-oxadiazoles," *ARKIVOC* 6: 82-90, 2002.
Kim et al., "Novel Oral Formulation of Paclitaxel Inhibits Neointimal Hyperplasia in a Rat Carotid Artery Injury Model," *Circulation* 109(12): 1558-1563, Mar. 8, 2004.
Kurzer and Douraghi-Zadeh, "Heterocyclic Compounds from Urea Derivatives. Part VI. Synthesis and Cyclisation of 1-Amino-3-(*NN'*-diarylamidino)guanidines and Some Analogues," *J. Chem. Soc.* 932-937, 1965.

Lebovic et al., "Peroxisome proliferator-activated receptor-gamma induces regression of endometrial explants in a rat model of endometriosis," *Fertility and Sterility* 82(Suppl 3): 1008-1013, Oct. 2004.
McCloskey et al., "Activation of the Axl Receptor Tyrosine Kinase Induces Mitogenesis and Transformation in 32D Cells," *Cell Growth & Differentiation* 5: 1105-1117, Oct. 1994.
McMahon, "VEGF Receptor Signaling in Tumor Angiogenesis," *The Oncologist* 5(suppl 1): 3-10, 2000.
Nakashima et al., "ApoE-Deficient Mice Develop Lesions of All Phases of Atherosclerosis Throughout the Arterial Tree," *Arterioscler. Thromb. Vasc. Biol.* 14(1): 133-140, Jan. 1994.
Nickoloff et al., "Severe Combined Immunodeficiency Mouse and Human Psoriatic Skin Chimeras. Validation of a New Animal Model," *American Journal of Pathology* 146(3): 580-588, Mar. 1995.
O'Donnell et al., "Expression of Receptor Tyrosine Kinase Axl and its Ligand Gas6 in Rheumatoid Arthritis," *American Journal of Pathology* 154(4): 1171-80, Apr. 1999.
Patani and LaVoie, "Bioisosterism: A Rational Approach in Drug Design," *Chem. Rev* 96: 3147-3176, 1996.
Peesapati and Venkata, "Synthesis and antimicrobial activity of new triazolo / tetrazolo-pyridazine [6,7] benzocycloheptenes," *Indian Journal of Chemistry* 41B: 839-844, Apr. 2002.
Phadke et al., "Evaluation of the Effects of Various Anti-Arthritic Drugs on Type II Collagen-Induced Mouse Arthritis Model," *Immunopharmacology* 10: 51-60, 1985.
Pinedo et al., "Translational Research: The Role of VEGF in Tumor Angiogenesis," *The Oncologist* 5(suppl 1): 1-2, 2000.
Reiter and Pongó, On Triazoles. "On Triazoles. VI [1]. The Acylation of 5-Amino-1,2,4-Triazoles," *J. Heterocyclic Chem.* 24(1): 127-142, Jan.-Feb. 1987.
Sarayba et al , "Inhibition of corneal neovascularization by a peroxisome proliferator-activated receptor-γ ligand," *Experimental Eye Research* 80: 435-442, 2005.
Sheets et al., "Cataract- and Lens-Specific Upregulation of ARK Receptor Tyrosine Kinase in Emory Mouse Cataract," *Investigative Ophthalmology & Visual Science* 43(6): 1870-1875, Jun. 2002.
Smith et al., "Oxygen-Induced Retinopathy in the Mouse," *Investigative Ophthalmology & Visual Science* 35(1): 101-111, Jan. 1994.
Somigliana et al., "Endometrial ability to implant in ectopic sites can be prevented by interleukin-12 in a murine model of endometriosis," *Human Reproduction* 14(12): 2944-2950, 1999.
Sun et al., "Coexpression of growth arrest-specific gene 6 and receptor tyrosine kinases, Axl and Sky, in human uterine endometrium and ovarian endometriosis," Molecular Human Reproduction 8 (6): 552-8, 2002.
Von Der Thüsen et al., "Adenoviral Transfer of Endothelial Nitric Oxide Synthase Attenuates Lesion Formation in a Novel Murine Model of Postangioplasty Restenosis," *Arterioscler. Thromb. Vasc. Biol.* 24: 357-362, Feb. 2004.
Wronski et al., "Endocrine and Pharmacological Suppressors of Bone Turnover Protect against Osteopenia in Ovariectomized Rats," *Endocrinology* 125(2): 810-816, 1989.
Xu et al., "Requirement for the tyrosine kinase Axl in angiogenesis and tumor growth," *Proc. Amer. Assoc. Cancer Res.* 46, 2005. Tumor Biology 14: Signaling and Angiogenesis; Abstract #2019 of observations disclosed at American Association Cancer Research General Meeting, Apr. 16-20, 2005, Anaheim, California, 1 page.
Yin et al., "Expression of growth arrest-specific gene 6 and its receptors in a rat model of chronic renal transplant rejection," *Transplantation* 73(4): 657-660, Feb. 27, 2002.

POLYCYCLIC HETEROARYL SUBSTITUTED TRIAZOLES USEFUL AS AXL INHIBITORS

CROSS-REFERENCE TO RELATED APPLICATIONS

This application is a continuation of U.S. patent application Ser. No. 13/725,407, filed Dec. 21, 2012 (now allowed); which is a continuation of U.S. patent application Ser. No. 13/002,487, filed Jan. 3, 2011 (now U.S. Pat. No. 8,349,838); which is a U.S. National Phase Application of International Application No. PCT/US2009/049617, filed Jul. 2, 2009; which claims the benefit of U.S. Provisional Patent Application No. 61/079,403, filed Jul. 9, 2008. These applications are incorporated herein by reference in their entirety.

FIELD OF THE INVENTION

This invention is directed to polycyclic heteroaryl substituted triazoles and pharmaceutical compositions thereof which are useful as inhibitors of the receptor protein tyrosine kinase known as Axl. This invention is also directed to methods of using the compounds and compositions in treating diseases and conditions associated with Axl activity, particularly in treating diseases and conditions associated with angiogenesis and/or cell proliferation.

BACKGROUND OF THE INVENTION

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (EC's) and vascular smooth muscle cells (VSMC's) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl-/- mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemia's. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoporosis, osteoarthritis and cataracts.

SUMMARY OF THE INVENTION

This invention is directed to certain polycyclic heteroaryl substituted triazoles which are useful as Axl inhibitors, methods of using such compounds in treating diseases and conditions associated with Axl activity and pharmaceutical compositions comprising such compounds.

Accordingly, in one aspect, this invention is directed to compounds of formula (I):

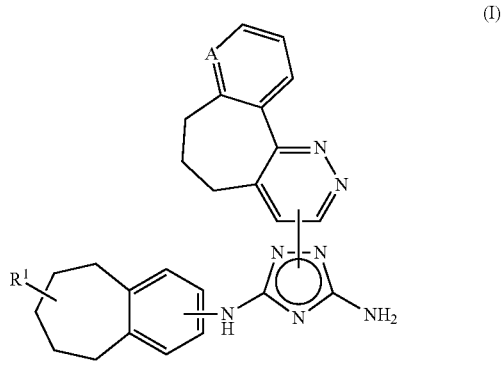

wherein:
A is =C(H)— or =N—;
$R^1$ is —N($R^2$)$R^3$, —N($R^2$)C(O)$R^3$ or —N($R^2$)—$R^4$—C(O)O$R^3$;

or $R^1$ is an N-heterocyclyl optionally substituted by one or more substituents selected from the group consisting of halo and —$R^4$—C(O)O$R^2$;

each $R^2$ and $R^3$ is hydrogen, alkyl, alkenyl, optionally substituted aralkyl, optionally substituted cycloalkyl, optionally substituted cycloalkylalkyl and optionally substituted heteroarylalkyl; and each $R^4$ is independently selected from the group consisting of a direct bond and an optionally substituted straight or branched alkylene chain;

as an isolated stereoisomer or mixture thereof, or a pharmaceutically acceptable salt thereof;

provided that the compound of formula (I) is not a compound selected from the group consisting of:

1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((bicyclo[2.2.1]heptan-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((bicyclo[2.2.1]heptan-2-yl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-azetidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-(R)-pyrrolidin-1-yl)-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-$N^3$-(7-diethylamino-6,7,8,9-tetrahydro-5H-benzo[7]annulene-2-yl)-1H-1,2,4-triazole-3,5-diamine.

In another aspect, this invention is directed to compounds of formula (II):

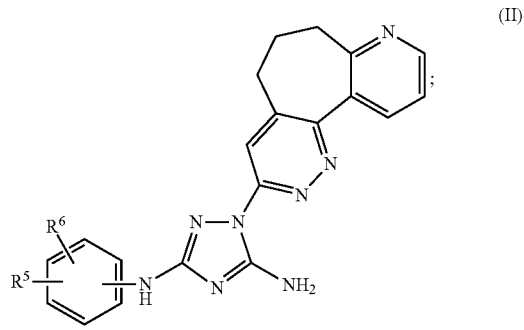

wherein:
$R^5$ is N-heterocyclyl optionally substituted by N-heterocyclyl; and
$R^6$ is halo;
as an isolated stereoisomer or mixture thereof, or a pharmaceutically acceptable salt thereof.

In another aspect, this invention is directed to pharmaceutical compositions comprising a pharmaceutically acceptable excipient and a compound of formula (I), as described above, as an isolated stereoisomer or mixture thereof, or a pharmaceutically acceptable salt thereof, or a compound of formula (II), as described above, as an isolated stereoisomer or mixture thereof, or a pharmaceutically acceptable salt thereof.

In another aspect, this invention is directed to methods of treating a disease or condition associated with Axl activity in a mammal, wherein the methods comprise administering to the mammal a therapeutically effective amount of a compound of formula (I), as described above, as an isolated stereoisomer or mixture thereof, or a pharmaceutically acceptable salt thereof, or a therapeutically effective amount of a pharmaceutical composition comprising a pharmaceutically acceptable excipient and a compound of formula (I), as described above, as an isolated stereoisomer or mixture thereof, or a pharmaceutically acceptable salt thereof, or a compound of formula (II), as described above, as an isolated stereoisomer or mixture thereof, or a pharmaceutically acceptable salt thereof, or a therapeutically effective amount of a pharmaceutical composition comprising a pharmaceutically acceptable excipient and a compound of formula (II), as described above, as an isolated stereoisomer or mixture thereof, or a pharmaceutically acceptable salt thereof.

In another aspect, this invention provides methods of preparing an (S)-enantiomer of the following formula:

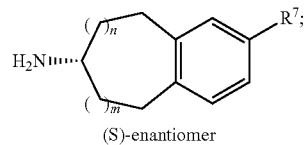

(S)-enantiomer where n and m are the same and are 0, 1 or 2;
$R^7$ is nitro, halo or —C(O)O$R^2$; and
$R^2$ is hydrogen, alkyl, alkenyl, optionally substituted aralkyl, optionally substituted cycloalkyl, optionally substituted cycloalkylalkyl and optionally substituted heteroaryl;
wherein the method comprises treating a compound of formula (i):

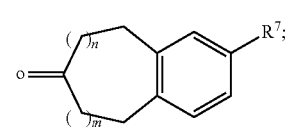

(i)

where n and m are the same and are 0, 1 or 2;
$R^7$ is nitro, halo or —C(O)O$R^2$; and
$R^2$ is hydrogen, alkyl, alkenyl, optionally substituted aralkyl, optionally substituted cycloalkyl, optionally substituted cycloalkylalkyl and optionally substituted heteroaryl;
with an amino donor molecule in the presence of a catalytic amount of a (S)-specific transaminase under suitable conditions to form the (S)-enantiomer.

In another aspect, this invention provides assays to determine a compound of the invention effectiveness in inhibiting Axl activity in a cell-based assay.

DETAILED DESCRIPTION OF THE INVENTION

Definitions

As used in the specification and appended claims, unless specified to the contrary, the following terms have the meaning indicated:

"Amino" refers to the —$NH_2$ radical.
"Carboxy" refers to the —C(O)OH radical.
"Cyano" refers to the —CN radical.

"Nitro" refers to the —NO$_2$ radical.
"Oxa" refers to the —O— radical.
"Oxo" refers to the =O radical.
"Thioxo" refers to the =S radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms ("lower alkyl"), and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

"Amino-donor molecule" refers to a organic molecule comprising a primary amine (—NH$_2$) group and which is suitable for the processes disclosed herein. Examples of amino-donor molecules include, but are not limited to, α-amino acids, such as alanine and phenylalanine, isopropylamine, 1-ethylpropylamine, 1,1,3,3-tetramethylbutylamine, 1,2-dimethylbutylamine, sec-butylamine, 1-phenylethylamine and the like.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical.

"Aralkyl" refers to a radical of the formula —R$_b$-R$_c$ where R$_b$ is an alkylene chain as defined above and R$_c$ is one or more aryl radicals as defined above, for example, benzyl, diphenylmethyl and the like.

"Cycloalkyl" refers to a stable non-aromatic monocyclic or polycyclic hydrocarbon radical consisting solely of carbon and hydrogen atoms, which may include spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms. Monocyclic cycloalkyl radicals include non-bridged cycloalkyl radicals, for example, cyclopropyl, cyclobutyl, cyclopentyl, cyclohexyl, cycloheptyl, and cyclooctyl. Polycyclic radicals include fused, spiro or bridged cycloalkyl radicals, for example, C$_{10}$ radicals such as adamantanyl (bridged) and decalinyl (fused), and C$_7$ radicals such as bicyclo[3.2.0]heptanyl (fused), norbornanyl and norbornenyl (bridged), as well as substituted polycyclic radicals, for example, substituted C$_7$ radicals such as bicyclo[2.2.1]heptenyl (bridged) and 7,7-dimethylbicyclo[2.2.1]heptanyl (bridged), and the like.

"Cycloalkylalkyl" refers to a radical of the formula —R$_b$R$_g$ where R$_b$ is an alkylene chain as defined above and R$_g$ is a cycloalkyl radical as defined above.

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purpose of this invention, the (S)-enantiomer of the invention is considered to be substantially free of the (R)-enantiomer when the (S)-enantiomer is present in enantiomeric excess of greater than 80%, preferably greater than 90%, more preferably greater than 95% and most preferably greater than 99%.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Heterocyclyl" refers to a stable 3- to 18-membered non-aromatic ring radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuranyl, thienyl[1,3] dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a] azepinyl, azepanyl, azabicyclo[3.2.1]octyl, and 2,7-diazaspiro[4.4]nonanyl.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro ring systems; and the nitrogen, carbon or sulfur atoms in the heteroaryl radical may be optionally oxidized; the nitrogen atom may be optionally quaternized. For purposes of this invention, the aromatic ring of the heteroaryl radical need not contain a heteroatom, as long as one ring of the heteroaryl radical contains a heteroatom. For example, 1,2,3,4-tetrahydroisoquinolin-7-yl is considered a "heteroaryl" for the purposes of this invention. Except for the polycyclic heteroaryls containing more than 14 ring atoms, as described above in the Summary of the Invention, a "heteroaryl" radical as defined herein can not contain rings having more than 7 members and cannot contain rings wherein two non-adjacent members thereof are connected through an atom or a group of atoms (i.e., a bridged ring system). Examples of heteroaryl radicals include, but are not limited to, azepinyl, acridinyl, benzimidazolyl, benzindolyl, 1,3-benzodioxolyl, benzofuranyl, benzooxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 1,2,3,4,5,6-hexahydrobenzo[d]azocin-8-yl, isothiazolyl, imidazolyl, indazolyl, indolyl, indazolyl, isoindolyl, indolinyl, isoindolinyl, isoquinolyl, indolizinyl, isoxazolyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, 5,6,7,8-tetrahydroquinazolinyl, 2,3,4,5-tetrahydrobenzo[b]oxepin-7-yl, 3,4-dihydro-2H-benzo[b][1,4]dioxepin-7-yl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, 1,2,3,4-tetrahydroisoquinolin-7-yl, triazinyl, thieno[2,3-d]pyrimidinyl, thieno[3,2-d]pyrimidinyl, thieno[2,3-c]pyridinyl, and thiophenyl (i.e., thienyl).

"Keto acid" refers to a carboxylic acid additionally containing a ketone functional group. An "2-keto acid" refers to a carboxylic acid wherein the ketone functional group is adjacent to the carboxylic acid (—C(O)OH) group.

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

"Transaminases" as used herein refers to naturally occurring or non-natural enzymes which catalyze the transfer of an amino group from an amino donor molecule to a ketone-containing molecule, preferably to a cyclic ketone fused to an aromatic ring, to produce an optically active molecule. Transaminases, or aminotransferases, have high stereoselectivity for a given enantiomer. Thus, the process of transamination utilizing a transaminase is a chiral synthesis, not a resolution.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For example, a compound of formula (II), as set forth above in the Summary of the Invention, where $R^5$ is 4-(4-(pyrrolidin-1-yl)piperidin-1-yl) and $R^6$ is 3-fluoro is named herein as 1-(6,7-dihydro-5H-pyrido[2',3':6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine.

For purposes of this invention, the depiction of the bond attaching the polycyclic substituent containing the $R^3$ substituent to the parent triazole moiety in formula (I), as shown below:

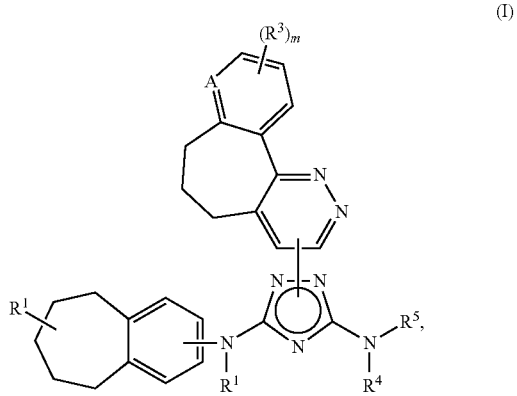

(I)

is intended to include only the four regioisomers shown below, i.e., compounds of formula (I-1), (I-2), (I-3) and (I-4):

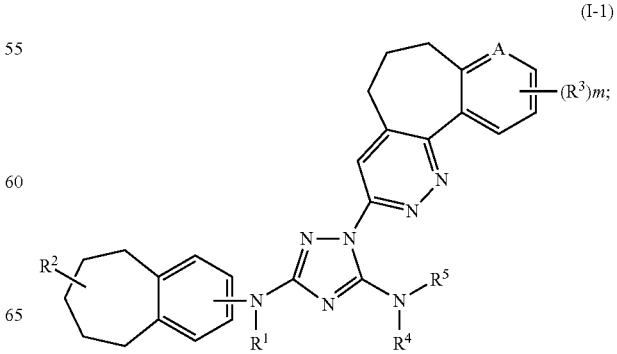

(I-1)

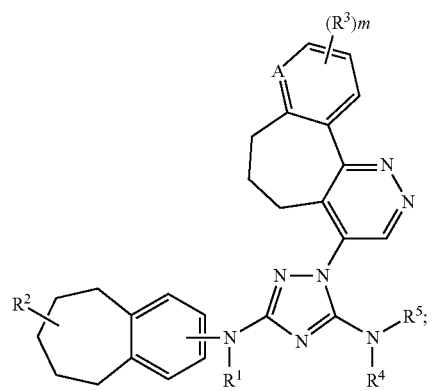

(I-2)

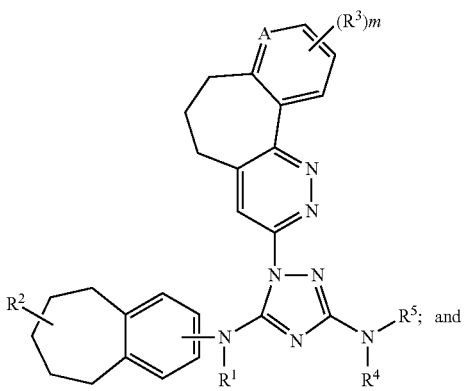

(I-3)

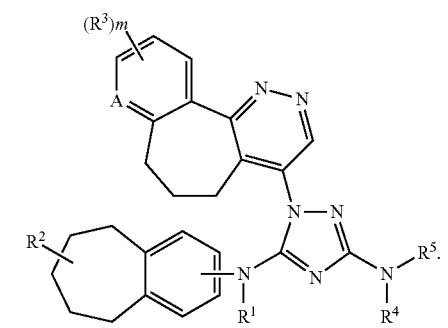

(I-4)

Embodiments of the Invention

Of the various aspects of the compounds of the invention, as set forth above in the Summary of the Invention, certain embodiments are preferred.

One embodiment of the invention is a compound of formula (I), as set forth above in the Summary of the Invention, as an isolated stereoisomer or mixture thereof, or a pharmaceutically acceptable salt thereof.

Another embodiment of the invention is where a compound of formula (I), as set forth above in the Summary of the Invention, is a compound of formula (Ia):

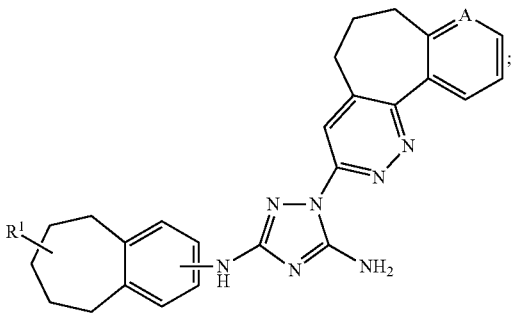

(Ia)

wherein:
A is =C(H)— or =N—;
$R^1$ is —N($R^2$)$R^3$, —N($R^2$)C(O)$R^3$ or —N($R^2$)—$R^4$—C(O) O$R^3$;
or $R^1$ is an N-heterocyclyl optionally substituted by one or more substituents selected from the group consisting of halo and —$R^4$—C(O)O$R^2$;
each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and
each $R^4$ is independently selected from the group consisting of a direct bond and an optionally substituted straight or branched alkylene chain,
as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =C(H)—;
$R^1$ is —N($R^2$)$R^3$, —N($R^2$)C(O)$R^3$ or —N($R^2$)—$R^4$—C(O) O$R^3$;
or $R^1$ is an N-heterocyclyl optionally substituted by one or more substituents selected from the group consisting of halo and —$R^4$—C(O)O$R^2$;
each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and each $R^4$ is independently selected from the group consisting of a direct bond and an optionally substituted straight or branched alkylene chain,
as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =C(H)—;
$R^1$ is —N($R^2$)$R^3$; and
$R^2$ and $R^3$ are each independently selected from the group consisting of hydrogen, alkyl, alkenyl, optionally substituted aralkyl, optionally substituted cycloalkyl, optionally substituted cycloalkylalkyl and optionally substituted heteroarylalkyl,
as an isolated stereoisomer or mixture thereof, or a pharmaceutically acceptable salt thereof.

Another embodiment of the invention is where a compound of formula (Ia), as set forth above, is a compound of formula (Ia1)

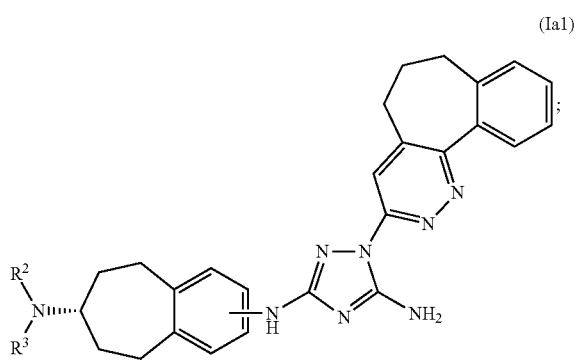

wherein:
R² and R³ are each independently selected from the group consisting of hydrogen, alkyl, alkenyl, optionally substituted aralkyl, optionally substituted cycloalkyl, optionally substituted cycloalkylalkyl and optionally substituted heteroarylalkyl.

Another embodiment of the invention is a compound of formula (Ia1), as set forth above, wherein R² and R³ are each independently selected from the group consisting of hydrogen, alkyl and alkenyl, as an isolated stereoisomer or mixture thereof, or a pharmaceutically acceptable salt thereof.

Another embodiment of the invention is a compound of formula (Ia1), as set forth above, selected from the group consisting of:

1-(6,7-dihydro-5H-benzo[6,7]cyclohepta[1,2-c]pyridazin-3-yl)-N³-((7S)-7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((2-methylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((propyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(dipropylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(diethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(2-propylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((3,3-dimethylbut-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(dimethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(3-pentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((2,2-dimethylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(3-methylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(3-methylbutyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(2-ethylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(but-2-enylamino)-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-N³-((7S)-7-(butyl(but-2-enyl)amino)-6,7,8,9-tetrahydro-5H-benzo[7]annulene-2-yl)-1H-1,2,4-triazole-3,5-diamine, as an isolated stereoisomer or mixture thereof, or a pharmaceutically acceptable salt thereof.

Another embodiment of the invention is a compound of formula (Ia1), as set forth above, wherein R² and R³ are each independently selected from the group consisting of hydrogen, optionally substituted cycloalkyl and optionally substituted cycloalkylalkyl, as an isolated stereoisomer or mixture thereof, or a pharmaceutically acceptable salt thereof.

Another embodiment of the invention is a compound of formula (Ia1), as set forth above, selected from the group consisting of:

1-(6,7-dihydro-5H-benzo[6,7]cyclohepta[1,2-c]pyridazin-3-yl)-N³-((7s)-7-(di(cyclopropylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclohexylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclopentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((1-cyclopentylethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclobutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7S)-7-(di(bicyclo[2.2.1]hept-2-en-5-ylmethyl)amino)-6,7,8,9-tetrahydro-5H-benzo[7]annulen-2-yl)-1H-1,2,4-triazole-3,5-diamine; and 1-(6,7-dihydro-5H-benzo[6,7]cyclohepta[1,2-c]pyridazin-3-yl)-$N^3$-((7S)-7-((bicyclo[2.2.1]hept-2-en-5-ylmethyl)amino)-6,7,8,9-tetrahydro-5H-benzo[7]annulen-2-yl)-1H-1,2,4-triazole-3,5-diamine, as an isolated stereoisomer or mixture thereof, or a pharmaceutically acceptable salt thereof.

Another embodiment of the invention is a compound of formula (Ia1), as set forth above, wherein $R^2$ and $R^3$ are each independently selected from the group consisting of hydrogen, optionally substituted aralkyl and optionally substituted heteroarylalkyl, as an isolated stereoisomer or mixture thereof, or a pharmaceutically acceptable salt thereof.

Another embodiment of the invention is a compound of formula (Ia1), as set forth above, selected from the group consisting of:

1-(6,7-dihydro-5H-benzo[6,7]cyclohepta[1,2-c]pyridazin-3-yl)-$N^3$-((7S)-7-((5-chlorothien-2-yl)methyl)amino-6,7,8,9-tetrahydro-5H-benzo[7]annulen-2-yl)-1H-1,2,4-triazole-3,5-diamine;

1-(6,7-dihydro-5H-benzo[6,7]cyclohepta[1,2-c]pyridazin-3-yl)-$N^3$-((7S)-7-((2-carboxyphenyl)methyl)amino-6,7,8,9-tetrahydro-5H-benzo[7]annulen-2-yl)-1H-1,2,4-triazole-3,5-diamine; and 1-(6,7-dihydro-5H-benzo[6,7]cyclohepta[1,2-c]pyridazin-3-yl)-$N^3$-((7S)-7-((3-bromophenyl)methyl)amino-6,7,8,9-tetrahydro-5H-benzo[7]annulen-2-yl)-1H-1,2,4-triazole-3,5-diamine, as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:

A is =C(H)—;
$R^1$ is —N($R^2$)C(O)$R^3$; and
$R^2$ and $R^3$ are each independently selected from the group consisting of hydrogen, alkyl, alkenyl, optionally substituted aralkyl, optionally substituted cycloalkyl, optionally substituted cycloalkylalkyl and optionally substituted heteroarylalkyl, as an isolated stereoisomer or mixture thereof, or a pharmaceutically acceptable salt thereof.

Another embodiment of the invention is where a compound of formula (Ia), as set forth above, is a compound of formula (Ia2):

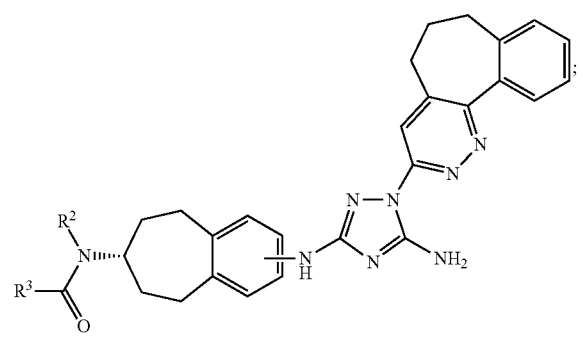

(Ia2)

wherein $R^2$ and $R^3$ are each independently selected from the group consisting of hydrogen and alkyl, as an isolated stereoisomer or mixture thereof, or a pharmaceutically acceptable salt thereof.

Another embodiment of the invention is a compound of formula (Ia2), as set forth above, which is 1-(6,7-dihydro-5H-benzo[6,7]cyclohepta[1,2-c]pyridazin-3-yl)-$N^3$-(7-(acetamido)-6,7,8,9-tetrahydro-5H-benzo[7]annulen-2-yl)-1H-1,2,4-triazole-3,5-diamine, as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:

A is =C(H)—;
$R^1$ is —N($R^2$)—$R^4$—C(O)O$R^3$;
$R^2$ and $R^3$ are each independently selected from the group consisting of hydrogen, alkyl, alkenyl, optionally substituted aralkyl, optionally substituted cycloalkyl, optionally substituted cycloalkylalkyl and optionally substituted heteroarylalkyl; and
$R^4$ is selected from the group consisting of a direct bond and an optionally substituted straight or branched alkylene chain, as an isolated stereoisomer or mixture thereof, or a pharmaceutically acceptable salt thereof.

Another embodiment of the invention is where a compound of formula (Ia), as set forth above, is a compound of formula (Ia3):

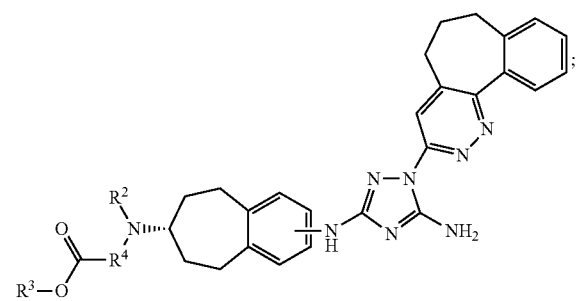

(Ia3)

wherein:
$R^2$ and $R^3$ are each independently selected from the group consisting of hydrogen and alkyl; and
$R^4$ is selected from the group consisting of a direct bond and a methylene chain, as an isolated stereoisomer or mixture thereof, or a pharmaceutically acceptable salt thereof.

Another embodiment of the invention is a compound of formula (Ia3), as set forth above, selected from the group consisting of:

1-(6,7-dihydro-5H-benzo[6,7]cyclohepta[1,2-c]pyridazin-3-yl)-$N^3$-(7-((methoxycarbonylmethyl)(methyl)amino)-6,7,8,9-tetrahydro-5H-benzo[7]annulen-2-yl)-1H-1,2,4-triazole-3,5-diamine;

1-(6,7-dihydro-5H-benzo[6,7]cyclohepta[1,2-c]pyridazin-3-yl)-$N^3$-(7-((carboxymethyl)(methyl)amino)-6,7,8,9-tetrahydro-5H-benzo[7]annulen-2-yl)-1H-1,2,4-triazole-3,5-diamine; and 1-(6,7-dihydro-5H-benzo[6,7]cyclohepta[1,2-c]pyridazin-3-yl)-$N^3$-((7S)-7-(t-butoxycarbonylamino)-6,7,8,9-tetrahydro-5H-benzo[7]annulen-2-yl)-1H-1,2,4-triazole-3,5-diamine, as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =C(H)—;
R$^1$ is an N-heterocyclyl optionally substituted by one or more substituents selected from the group consisting of halo and —R$^4$—C(O)OR$^2$; and
R$^2$ is selected from the group consisting of hydrogen, alkyl, alkenyl, optionally substituted aralkyl, optionally substituted cycloalkyl, optionally substituted cycloalkylalkyl and optionally substituted heteroarylalkyl,
as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =C(H)—;
R$^1$ is pyrrolidinyl, piperidinyl or piperazinyl, each independently optionally substituted by one or more substituents selected from the group consisting of halo and —R$^4$—C(O)OR$^2$; and
R$^2$ is selected from the group consisting of hydrogen and alkyl,
as an isolated stereoisomer or mixture thereof, or a pharmaceutically acceptable salt thereof.

Another embodiment of the invention is a compound of formula (Ia), as set forth above, selected from the group consisting of:
1-(6,7-dihydro-5H-benzo[6,7]cyclohepta[1,2-c]pyridazin-3-yl)-N$^3$-(7-((2R)-2-(methoxycarbonyl)pyrrolidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-(4,4-difluoropiperidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-((2R)-2-(carboxy)pyrrolidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-(4-(ethoxycarbonyl)piperidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-(4-(carboxy)piperidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-(4-(ethoxycarbonylmethyl)piperazin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N$^3$-(7-(4-(carboxymethyl)piperazin-1-yl)-6,7,8,9-tetrahydro-5H-benzo[7]annulene-2-yl)-1H-1,2,4-triazole-3,5-diamine; and
1-(6,7-dihydro-5H-benzo[6,7]cyclohepta[1,2-c]pyridazin-3-yl)-N$^3$-(7-(pyrrolidin-1-yl)-6,7,8,9-tetrahydro-5H-benzo[7]annulene-1-yl)-1H-1,2,4-triazole-3,5-diamine,
as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =N—;
R$^1$ is —N(R$^2$)R$^3$, —N(R$^2$)C(O)R$^3$ or —N(R$^2$)—R$^4$—C(O)OR$^3$;
or R$^1$ is an N-heterocyclyl optionally substituted by one or more substituents selected from the group consisting of halo and —R$^4$—C(O)OR$^2$;
each R$^2$ and R$^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and
each R$^4$ is independently selected from the group consisting of a direct bond and an optionally substituted straight or branched alkylene chain,
as an isolated stereoisomer or mixture thereof, or a pharmaceutically acceptable salt thereof.

Another embodiment of the invention is where a compound of formula (I), as set forth above in the Summary of the Invention, is a compound of formula (Ia), as set forth above, wherein:
A is =N—;
R$^1$ is —N(R$^2$)—R$^4$—C(O)OR$^3$,
each R$^2$ and R$^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and
each R$^4$ is independently selected from the group consisting of a direct bond or an optionally substituted straight or branched alkylene chain,
as an isolated stereoisomer or mixture thereof, or a pharmaceutically acceptable salt thereof.

Another embodiment of the invention is where a compound of formula (Ia), as set forth above, is a compound of formula (Ia4):

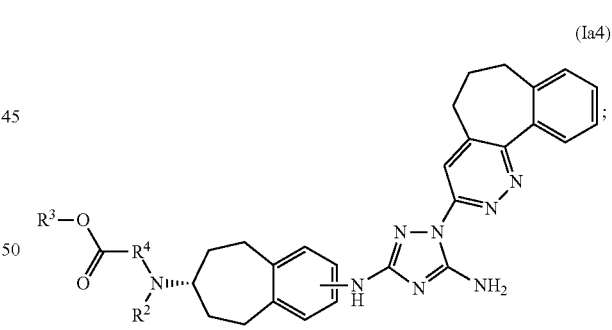

(Ia4)

wherein:
R$^2$ and R$^3$ are each independently selected from the group consisting of hydrogen and alkyl; and
R$^4$ is a direct bond or a methylene chain,
as an isolated stereoisomer or mixture thereof, or a pharmaceutically acceptable salt thereof.

Another embodiment of the invention is a compound of formula (Ia3), as set forth above, which is 1-(6,7-dihydro-5H-pyrido[2',3':6,7]cyclohepta[1,2-c]pyridazin-3-yl)-N$^5$-((7S)-7-(t-butoxycarbonylamino)-6,7,8,9-tetrahydro-5H-benzo[7]annulene-2-yl)-1H-1,2,4-triazole-3,5-diamine, as an isolated stereoisomer or mixture thereof, or a pharmaceutically acceptable salt thereof.

Another embodiment of the invention is where a compound of formula (Ia), as set forth above, is a compound of formula (Ia5):

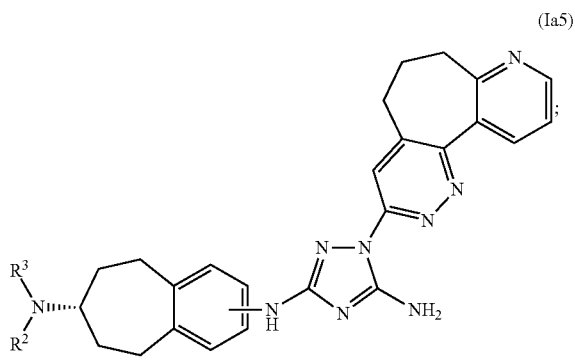

(Ia5)

wherein:
$R^2$ and $R^3$ are each independently selected from the group consisting of hydrogen, alkyl, cycloalkyl and cycloalkylalkyl,
as an isolated stereoisomer or mixture thereof, or a pharmaceutically acceptable salt thereof.

Another embodiment of the invention is a compound of formula (Ia5), as set forth above, selected from the group consisting of:
1-(6,7-dihydro-5H-pyrido[2',3':6,7]cyclohepta[1,2-c]pyridazin-3-yl)-$N^3$-((7S)-7-amino-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(dimethylamino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(diethylamino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(dipropylamino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(di(cyclopropylmethyl)amino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(di(3-methylbutyl)amino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(cyclobutylamino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(cyclohexylamino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-((methylethyl)amino)-6,7,8,9-tetrahydro-5H-benzo[7]annulen-2-yl)-1H-1,2,4-triazole-3,5-diamine;
1-(6,7-dihydro-5H-pyrido[2',3':6,7]cyclohepta[1,2-c]pyridazin-3-yl)-$N^3$-((7S)-7-(cyclopentylamino)-6,7,8,9-tetrahydro-5H-benzo[7]annulen-2-yl)-1H-1,2,4-triazole-3,5-diamine; and
1-(6,7-dihydro-5H-pyrido[2',3':6,7]cyclohepta[1,2-c]pyridazin-3-yl)-$N^3$-((7S)-7-(2-butylamino)-6,7,8,9-tetrahydro-5H-benzo[7]annulen-2-yl)-1H-1,2,4-triazole-3,5-diamine,
as an isolated stereoisomer or mixture thereof, or a pharmaceutically acceptable salt thereof.

Another embodiment of the invention is where a compound of formula (I), as set forth above in the Summary of the Invention, is a compound of formula (Ib):

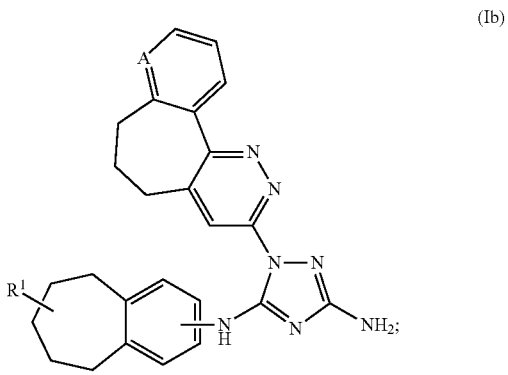

(Ib)

wherein:
A is =C(H)— or =N—;
$R^1$ is —N($R^2$)$R^3$, —N($R^2$)C(O)$R^3$ or —N($R^2$)—$R^4$—C(O)O$R^3$;
or $R^1$ is an N-heterocyclyl optionally substituted by one or more substituents selected from the group consisting of halo and —$R^4$—C(O)O$R^2$;
each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and
each $R^4$ is independently selected from the group consisting of a direct bond and an optionally substituted straight or branched alkylene chain; and
as an isolated stereoisomer or mixture thereof, or a pharmaceutically acceptable salt thereof,
as an isolated stereoisomer or mixture thereof, or a pharmaceutically acceptable salt thereof.

Another embodiment of the invention is where a compound of formula (I), as set forth above in the Summary of the Invention, is a compound of formula (Ib), as set forth above, wherein:
A is =C(H)—;
$R^1$ is —N($R^2$)$R^3$, —N($R^2$)C(O)$R^3$ or —N($R^2$)—$R^4$—C(O)O$R^3$;
or $R^1$ is an N-heterocyclyl optionally substituted by one or more substituents selected from the group consisting of halo and —$R^4$—C(O)O$R^2$;
each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroarylalkyl; and
each $R^4$ is independently selected from the group consisting of a direct bond and an optionally substituted straight or branched alkylene chain,
as an isolated stereoisomer or mixture thereof, or a pharmaceutically acceptable salt thereof.

Another embodiment of the invention is where a compound of formula (I), as set forth above in the Summary of the Invention, is a compound of formula (Ib), as set forth above, wherein:

A is =C(H)—;
$R^1$ is —N($R^2$)—$R^4$—C(O)O$R^3$;
$R^2$ and $R^3$ are each independently selected from the group consisting of hydrogen, alkyl, alkenyl, optionally substituted aralkyl, optionally substituted cycloalkyl, optionally substituted cycloalkylalkyl and optionally substituted heteroarylalkyl; and
$R^4$ is selected from the group consisting of a direct bond and an optionally substituted straight or branched alkylene chain, as an isolated stereoisomer or mixture thereof, or a pharmaceutically acceptable salt thereof.

Another embodiment of the invention is where a compound of formula (Ib), as set forth above, is a compound of formula (Ib1):

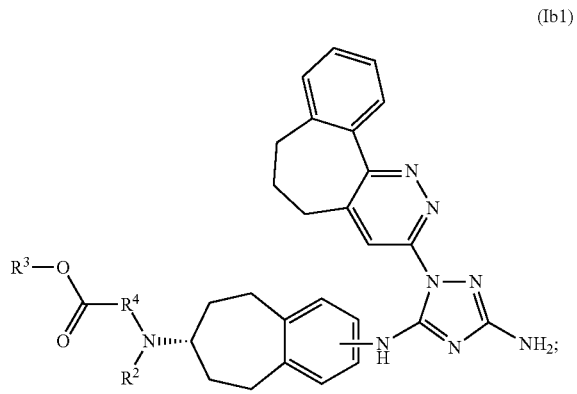

(Ib1)

wherein:
$R^2$ and $R^3$ are each independently selected from the group consisting of hydrogen and alkyl; and
$R^4$ is selected from the group consisting of a direct bond and a methylene chain, as an isolated stereoisomer or mixture thereof, or a pharmaceutically acceptable salt thereof.

Another embodiment of the invention is a compound of formula (Ib1), as set forth above, which is 1-(6,7-dihydro-5H-benzo[6,7]cyclohepta[1,2-c]pyridazin-3-yl)-$N^5$-((7S)-7-(t-butoxycarbonylamino)-6,7,8,9-tetrahydro-5H-benzo[7]annulene-2-yl)-1H-1,2,4-triazole-3,5-diamine, as an isolated stereoisomer or mixture thereof, or a pharmaceutically acceptable salt thereof.

Another embodiment of the invention is where a compound of formula (I), as set forth above in the Summary of the Invention, is a compound of formula (Ib), as set forth above, wherein:

A is =C(H)—;
$R^1$ is an N-heterocyclyl optionally substituted by one or more substituents selected from the group consisting of halo and —$R^4$—C(O)O$R^2$; and
$R^2$ is selected from the group consisting of hydrogen, alkyl, alkenyl, optionally substituted aralkyl, optionally substituted cycloalkyl, optionally substituted cycloalkylalkyl and optionally substituted heteroarylalkyl, as an isolated stereoisomer or mixture thereof, or a pharmaceutically acceptable salt thereof.

Another embodiment of the invention is where a compound of formula (I), as set forth above in the Summary of the Invention, is a compound of formula (Ib), as set forth above, wherein:

A is =C(H)—;
$R^1$ is pyrrolidinyl optionally substituted by one or more substituents selected from the group consisting of halo and —$R^4$—C(O)O$R^2$; and
$R^2$ is selected from the group consisting of hydrogen and alkyl, as an isolated stereoisomer or mixture thereof, or a pharmaceutically acceptable salt thereof.

Another embodiment of the invention is a compound of formula (Ib), as set forth above, which is 1-(6,7-dihydro-5H-benzo[6,7]cyclohepta[1,2-c]pyridazin-3-yl)-$N^5$-(7-(pyrrolidin-1-yl)-6,7,8,9-tetrahydro-5H-benzo[7]annulene-1-yl)-1H-1,2,4-triazole-3,5-diamine, as an isolated stereoisomer or mixture thereof, or a pharmaceutically acceptable salt thereof.

Another embodiment of the invention is a compound of formula (II), as set forth above in the Summary of the Invention, as an isolated stereoisomer or mixture thereof, or a pharmaceutically acceptable salt thereof.

Another embodiment of the invention is a compound of formula (II), as set forth above in the Summary of the Invention, wherein:
$R^5$ is piperidinyl substituted by pyrrolidinyl; and
$R^6$ is halo, as an isolated stereoisomer or mixture thereof, or a pharmaceutically acceptable salt thereof.

Another embodiment of the invention is a compound of formula (II), as set forth above in the Summary of the Invention, which is 1-(6,7-dihydro-5H-pyrido[2',3':6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine, as an isolated stereoisomer or mixture thereof, or a pharmaceutically acceptable salt thereof.

Another embodiment of the invention is a method of preparing an (S)-enantiomer of the following formula:

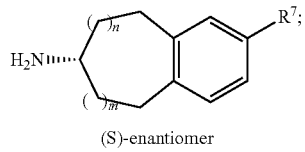

(S)-enantiomer as set forth above in the Summary of the Invention.

Another embodiment of the invention is a method of preparing an (S)-enantiomer of the following formula:

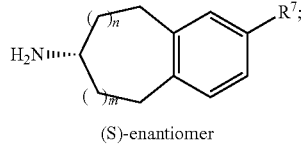

(S)-enantiomer as set forth above in the Summary of the Invention, wherein the compound of formula (i) is a compound of formula (Cb-1):

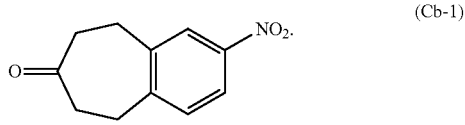 [SMILES: O=C1CCc2ccc([N+](=O)[O-])cc2CC1]

(Cb-1)

Another embodiment of the invention is a method of preparing an (S)-enantiomer of the following formula:

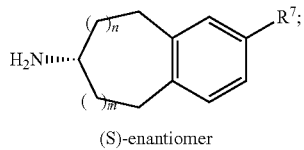

(S)-enantiomer as set forth above in the Summary of the Invention, wherein the (S)-enantiomer is a compound of formula (Cb-2):

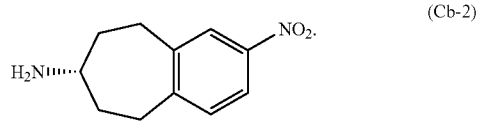 [SMILES: N[C@H]1CCc2ccc([N+](=O)[O-])cc2CC1]

Another embodiment of the invention is a method of preparing an (S)-enantiomer of the following formula:

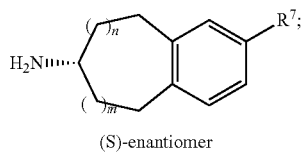

(S)-enantiomer as set forth above in the Summary of the Invention, wherein the (S)-enantiomer is formed in greater than 80% ee.

Of the various aspects of the pharmaceutical compositions of the invention comprising a pharmaceutically acceptable excipient and a compound of the invention, as set forth above in the Summary of the Invention, certain embodiments are preferred.

One embodiment of these pharmaceutical compositions is wherein the compound of the invention therein is selected from any one embodiment of the compounds of the invention, as set forth above, or from any combination of embodiments of the compounds of the invention, as set forth above.

Of the various aspects of methods of treating a disease or condition associated with Axl activity in a mammal, wherein the method comprises administering to a mammal in need thereof a therapeutically effective amount of a compound the invention, certain embodiments are preferred.

One embodiment of these methods is the method wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoarthritis and cataracts.

One embodiment of these methods is the method wherein a manifestation of the disease or condition is solid tumor formation in said mammal.

One embodiment of these methods is the method wherein the disease or condition is selected from the group consisting of breast carcinoma, renal carcinoma, endometrial carcinoma, ovarian carcinoma, thyroid carcinoma, non-small cell lung carcinoma, and uveal melanoma.

One embodiment of these methods is the method wherein a manifestation of the disease or condition is liquid tumor formation in said mammal.

One embodiment of these methods is the method wherein the disease or condition is myeloid leukemia or lymphoma.

One embodiment of these methods is the method wherein the disease or condition is endometriosis.

One embodiment of these methods is the method wherein the disease or condition is metastasis to the liver.

One embodiment of these methods is the method wherein the compounds of invention utilized therein is selected from any one embodiment of the compounds of the invention, as set forth above, or from any combination of embodiments of the compounds of the invention, as set forth above.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of rheumatoid arthritis, vascular disease/injury (including but not limited to restenosis, atherosclerosis and thrombosis), psoriasis, visual impairment due to macular degeneration, diabetic retinopathy or retinopathy of prematurity, kidney disease (including but not limited to glomerulonephritis, diabetic nephropathy and renal transplant rejection), osteoarthritis and cataracts.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of breast carcinoma, renal carcinoma, endometrial carcinoma, ovarian carcinoma, thyroid carcinoma, non-small cell lung carcinoma, uveal melanoma, myeloid leukemia and lymphoma.

Another embodiment of the invention are those methods of treating a disease or condition associated with Axl activity by administering to the mammal of therapeutically effective amount of a pharmaceutical composition of the invention, as set forth above in the Summary of the Invention, wherein the disease or condition is endometriosis.

Specific embodiments of the invention are described in more detail in the following sections.

Utility and Testing of the Compounds of the Invention

The oncogenic RTK, Axl, was recently identified, using a retroviral-based functional genetic screening protocol, as a regulator of haptotactic migration, which is a key event in angiogenesis. Axl inhibition by RNAi-mediated silencing blocked endothelial cell migration, proliferation and in vitro tube formation. These observations, which were disclosed at the American Association Cancer Research General Meeting, Apr. 16-20, 2005, Anaheim, Calif., and The 7th Annual Symposium on Anti-Angiogenic Agents, Feb. 10-13, 2005, San Diego, Calif.; (*Requirement for The Receptor Tyrosine Kinase Axl in Angiogenesis and Tumor Growth*, Holland, S. J. Powell, M. J., Franci, C., Chan, E., Friera, A. M., Atchison, R., Xu, W., McLaughlin, J., Swift, S. E., Pali, E., Yam, G., Wong, S., Xu, X., Hu, Y., Lasaga, J., Shen, M., Yu, S., Daniel, R., Hitoshi, Y., Bogenberger, J., Nor, J. E., Payan, D. G and Lorens, J. B), were substantiated by an in vivo study which demonstrated that stable, shRNAi-mediated Axl knockdown impaired formation of functional human blood vessels in a mouse model of human angiogenesis. These observations were published in a peer reviewed journal (Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. "Multiple roles for the receptor tyrosine kinase axl in tumor formation." *Cancer Res.* (2005) Vol 65 pp 9294-303. These observations are also disclosed in U.S. Published Patent Application 2005/0118604 and European Patent Application 1 563 094, the disclosures of which are incorporated in full by reference. Axl signaling, therefore, impacts multiple functions required for neovascularization in vitro, and regulates angiogenesis in vivo. Regulation of these pro-angiogenic processes required the catalytic activity of Axl. Thus, Axl-mediated angiogenic stimulation would be amenable to modulation by a small molecule inhibitor of Axl catalytic activity.

Accordingly, the compounds of the invention are small molecule inhibitors of Axl catalytic activity, and are therefore useful in treating diseases and conditions which are associated with Axl catalytic activity including those diseases and conditions which are characterized by angiogenesis and/or cell proliferation. In particular, the compounds of the invention and pharmaceutical compositions of the invention are useful in treating diseases and conditions which are alleviated by the modulation of Axl activity. For purposes of this invention, diseases and conditions which are alleviated by the "modulation of Axl activity" includes diseases and conditions which are alleviated by a decrease in Axl activity and diseases and conditions which are alleviated by an increase in Axl activity. Preferably such diseases and conditions are alleviated by a decrease in Axl activity. Diseases and conditions which are alleviated by the modulation of Axl activity include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts.

In addition to the foregoing, the compounds of the invention are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostatsis as manifested in osteoporosis or osteoarthritis; viral infection as manifested, for example, in ebola virus infection; or differentiation as manifested in obesity. The compounds of the invention may also be used to modulate inflammatory processes by treating sepsis, acting as vaccine adjuvants, and/or potentiating the immune response in immuno-compromised patients.

In one embodiment, the compounds of the invention are effective in treating metastasis to the liver. For example, treatment with compounds of the invention can result in pronounced reduction in the development of liver micrometastases. One method of the invention is treatment of a patient with compounds of the invention to reduce metastasis to the liver. This method can be done with compounds of the invention alone or in combination with other agents to produce the desired therapeutic benefit.

The compounds of the invention are also useful in treating cell proliferative disorders. A cell proliferative disorder refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds of the invention relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

Therefore, in addition to the foregoing, the compounds of the invention are useful in treating renal cell carcinoma, clear cell carcinoma of kidney, and renal cell adenocarcinoma; invasive ductal carcinoma, invasive lobular carcinoma, ductal carcinoma, lobular carcinoma in situ, and metastatic breast cancer; basal cell carcinoma, squamous cell carcinoma, malignant melanoma, and Karposi's sarcoma; small cell and non-small cell lung carcinoma, bronchial adema, pleuropulmonary blastoma, and malignant mesothelioma; brain stem and hyptothalamic glioma, cerebellar and cerebral astrocytoma, medullablastoma, ependymal tumors, oligodendroglial, meningiomas, and neuroectodermal and pineal tumors; prostate cancer, testicular cancer, and penile cancer; uterine cancer (endometrial), cervical, ovarian, vaginal, vulval cancers, uterine sarcoma, ovarian germ cell tumor; anal, colon, colorectal, esophageal, gallbladder, stomach (gastric), pancreatic cancer, pancreatic cancer-Islet cell, rectal, small-intestine, and salivary gland cancers; hepatocellular carcinoma, cholangiocarcinoma, mixed hepatocellular cholangiocarcinoma, and primary liver cancer; intraocular melanoma, retinoblastoma, and rhabdomyosarcoma; laryngeal, hypopharyngeal, nasopharyngeal, oropharyngeal cancers, and lip and oral cancer; squamous neck cancer; metastatic paranasal sinus cancer; B cell and C cell lymphomas, non-Hodgkins lymphoma, cutaneous T cell lymphoma, Hodgkins disease, and lymphoma of the central nervous system; acute myelogenous (myeloid) leukemia, acute lymphoblastic leukemia, chronic lymphocytic leukemia, chronic myelogenous leukemia, and hairy cell leukemia; thyroid cancer, thymoma, and malignant thymoma; bladder cancer; and sarcoma of the soft tissue, osteosarcoma, malignant fibrous histiocytoma, lymphosarcoma, and rhabdomyosarcoma.

Of the B cell lymphoma group of diseases and conditions, the compounds of the invention are useful in treating precursor B-lymphoblastic leukemia/lymphoma (precursor B-cell acute lymphoblastic leukemia), B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia Of the T cell lymphoma group of diseases and conditions, the compounds of the invention are useful in treating precursor T-lymphoblastic lymphoma/leukemia (precursor T-cell acute lymphoblastic leukemia), T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma not otherwise characterized, angioimmunoblastic T-cell lymphoma, anaplastic large-cell lymphoma, T/null cell, primary systemic type.

Of the Hodgkins disease group, the compounds of the invention are useful in treating nodular lymphocyte-predominant Hodgkin's lymphoma, nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma.

The compounds of the invention are also useful in treating myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia, chronic myelomonocytic leukemia, atypical chronic myelogenous leukemia, and juvenile myelomonocytic leukemia, refractory anemia (with ringed sideroblasts and without ringed sideroblasts), refractory cytopenia (myelodysplastic syndrome) with multilineage dysplasia, refractory anemia (myelodysplastic syndrome) with excess blasts, 5q-syndrome, and myelodysplastic syndrome with t(9;12)(q22; p12).

The compounds of the invention are also useful in treating acute myelogenous leukemia with t(8;21)(q22;q22), AML1 (CBF-alpha)/ETO, acute promyelocytic leukemia (AML with t(15;17)(q22;q11-12) and variants, PML/RAR-alpha), acute myelogenous leukemia with abnormal bone marrow eosinophils (inv(16)(p13q22) or t(16;16)(p13;q11), CBFb/MYH11X), and acute myelogenous leukemia with 11q23 (MLL) abnormalities, acute myelogenous leukemia minimally differentiated, acute myelogenous leukemia without maturation, acute myelogenous leukemia with maturation, acute myelomonocytic leukemia, acute monocytic leukemia, acute erythroid leukemia, acute megakaryocytic leukemia, acute basophilic leukemia, and acute panmyelosis with myelofibrosis.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human Axl-expressing cancer cell lines including, but not limited to, HeLa, MDA-MB-231, SK-OV-3, OVCAR-8, DU145, H1299, ACHN, A498 and Caki-1.

The compounds of the invention may be tested for their use in treating leukemias in the xenograft in SCID or nu/nu mouse model using human Axl-expressing AML and CML leukemia cell lines.

The compounds of the invention may be tested for their use in treating endometriosis by using the syngenic mouse model of endometriosis (see Somigliana, E. et al., "Endometrial ability to implant in ectopic sites can be prevented by interleukin-12 in a murine model of endometriosis", *Hum. Reprod.* (1999), Vol. 14, NO. 12, pp. 2944-50). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", *Fertil. Steril.* (2004), 82 Suppl 3, pp. 1008-13).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", *Circulation* (2004), Vol. 109, No. 12, pp. 1558-63, Epub 2004 Mar. 8).

The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", *Arterioscler. Thromb. Vasc. Biol.* (2004), Vol. 24, No. 2, pp. 357-62).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", *Arterioscler. Thromb.* (1994), Vol. 14, No. 1, pp. 133-40).

The compounds of the invention may also be tested for their use in treating thrombosis using the collagen-epinephrin-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", *J Clin Invest*. (2005) Vol 115 pp 237-46).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", *Am. J. Pathol.* (1995), Vol. 146, No. 3, pp. 580-8).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. *Exp Eye Res.* 2005 March; 80(3):435-42) or the laser-induced mouse choroidal neovasculation model (see Bora, P. S., et al., "Immunotherapy for choroidal neovascularization in a laser-induced mouse model simulating exudative (wet) macular degeneration", *Proc. Natl. Acad. Sci. U.S.A.* (2003), Vol. 100, No. 5, pp. 2679-84, Epub 2003 Feb. 14).

The compounds of the invention may be tested for their use in treating retinopathy of prematurity in the mouse retinopathy of prematurity model (see Smith, L. E. et al., "Oxygen-induced retinopathy in the mouse", *Invest. Ophthalmol. Vis. Sci.* (1994), Vol. 35, No. 1, pp. 101-11).

The compounds of the invention may be tested for their use in treating glomerulonephritis or diabetic nephropathy in the rat anti-Thy1.1-induced experimental mesengial proliferative glomerulonephritis model (see Smith, L. E. et al. cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", *Transplantation* (2002), Vol. 73, No. 4, pp. 657-60).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", *Immunopharmacology* (1985), Vol. 10, No. 1, pp. 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", *Arthritis. Rheum.* (1998), Vol. 41, No. 9, pp. 1639-44).

The compounds of the invention may be tested for their use in treating osteoporosis by using the ovariectomized rat model (see Wronski, T. J. et al., "Endocrine and pharmacological suppressors of bone turnover protect against osteopenia in ovariectomized rats", *Endocrinology* (1989), Vol. 125, no. 2, pp 810-6) or the ovariectomized mouse model (see Alexander, J. M. et al., "Human parathyroid hormone 1-34 reverses bone loss in ovariectomized mice", *J Bone Miner Res.* (2001), Vol. 16, no. 9, pp 1665-73; Fujioka, M. et al., "Equol, a metabolite of daidzein, inhibits bone loss in ovariectomized mice", *J Nutr.* (2004), Vol. 134, no. 10, pp 2623-7).

The compounds of the invention may be tested for their use in treating cataracts by using the $H_2O_2$-induced model (see Kadoya, K. et al., "Role of calpain in hydrogen peroxide induced cataract", *Curr. Eye Res.* (1993), Vol. 12, No. 4, pp. 341-6) or the Emory mouse model (see Sheets, N. L. et al., "Cataract- and lens-specific upregulation of ARK receptor tyrosine kinase in Emory mouse cataract", *Invest. Ophthalmol. Vis. Sci.* (2002), Vol. 43, No. 6, pp. 1870-5).

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Schemes illustrate methods to make compounds of this invention, e.g., compounds of formula (I):

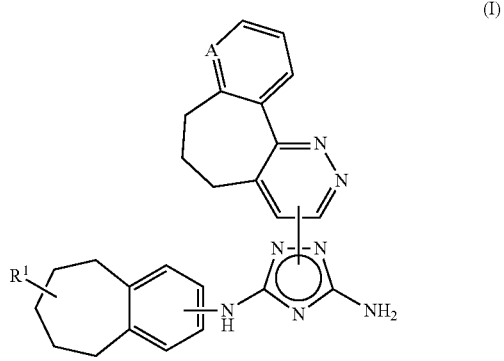

(I)

where A and R$^1$ are described above in the Summary of the Invention for compounds of formula (I), as isolated stereoisomers or mixtures thereof, as tautomers or mixtures thereof, or as pharmaceutically acceptable salts. In particular, the following Reaction Schemes illustrate methods to make compounds of formula (I) having the following formula (Ia):

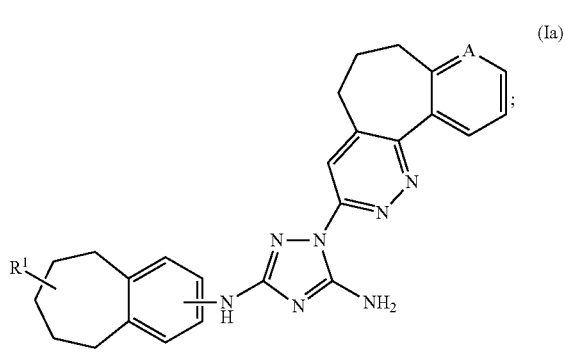

wherein:

A is =C(H)— or =N—;

$R^1$ is —N($R^2$)$R^3$, —N($R^2$)C(O)$R^3$, —N($R^2$)—$R^4$—C(O)O$R^3$, or $R^1$ is an N-heterocyclyl optionally substituted by one or more substituents selected from the group consisting of halo and —$R^4$—C(O)O$R^2$, each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroaryl; and each $R^4$ is independently selected from the group consisting of a direct bond or an optionally substituted straight or branched alkylene chain; and as an isolated stereoisomer or mixture thereof, or a pharmaceutically acceptable salt thereof.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) and the compounds of formula (II), as set forth above in the Summary of the Invention, not specifically illustrated below by using the appropriate starting components and modifying the parameters of the synthesis as needed.

It is also understood that in the following Reaction Schemes and throughout this description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters.

Protecting groups may be added or removed in accordance with standard techniques, which are known to one of ordinary skill in the art and as described herein.

The use of protecting groups is described in detail in Green, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs".

In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention. $^1$H NMR spectra were recorded in CDCl$_3$, DMSO-d$_6$, CD$_3$OD, Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

Compounds of formula (Ia), as described above, are generally prepared as illustrated below in Reaction Scheme 1 where A and $R^1$ are as described above for the compounds of formula (Ia) and Ph is a phenyl group:

REACTION SCHEME 1

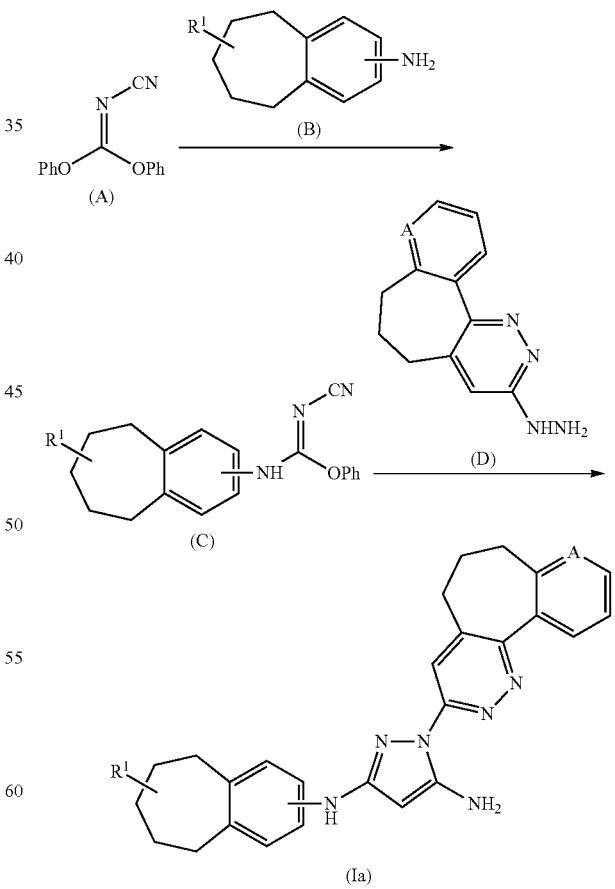

Compounds of formula (A), formula (B) and formula (D) are commercially available or can be prepared by methods known to one skilled in the art or by methods disclosed herein.

In general, compounds of formula (Ia) are prepared, as set forth by Reaction Scheme 1, by first treating a compound of formula (A) (where the phenyl groups therein may be replaced with other suitable groups or suitably substituted groups known to one skilled in the art) (1.1 equiv) with an equivalent amount of an aniline of formula (B) in an polar solvent, including, but not limited to, isopropyl alcohol, at ambient temperatures overnight. The diarylisourea product of formula (C) generally precipitates and isolation can be accomplished via filtration, washing with an appropriate solvent, and drying. Hydrazine hydrate of formula (D) (2 equivalents) is added to a slurry of the compound of formula (C) in an alcohol or other appropriate solvent. Generally, the ring formation reaction occurs at ambient temperature and the product triazole of formula (Ia) can be isolated by standard isolation techniques. Compounds of formula (Ia) can be subsequently treated with an appropriately substituted alkylating or acylating agent under standard conditions to form compounds of formula (I), as set forth in the Summary of the Invention, wherein $R^2$ and $R^3$ in the compounds so prepared are as described above in the Summary of the Invention for compounds of formula (I).

Compounds of formula (Ib), which are compounds of formula (I) having the following formula (Ib):

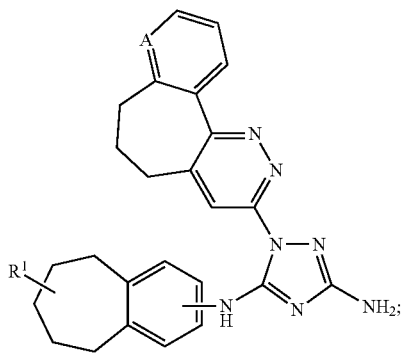

(Ib)

wherein:
A is =C(H)— or =N—;
$R^1$ is —N($R^2$)$R^3$, —N($R^2$)C(O)$R^3$, —N($R^2$)—$R^4$—C(O)O$R^3$,
or $R^1$ is an N-heterocyclyl optionally substituted by one or more substituents selected from the group consisting of halo and —$R^4$—C(O)O$R^2$,
each $R^2$ and $R^3$ is independently selected from the group consisting of hydrogen, alkyl, alkenyl, optionally substituted aralkyl, optionally substituted cycloalkyl, optionally substituted cycloalkylalkyl and optionally substituted heteroaryl; and
each $R^4$ is independently selected from the group consisting of a direct bond or an optionally substituted straight or branched alkylene chain; and
as an isolated stereoisomer or mixture thereof, or a pharmaceutically acceptable salt thereof;
can be prepared using the synthetic route outlined in Reaction Scheme 1 in varying amounts depending on the steric and electronic nature of the starting materials as well as the particular reaction conditions employed. In some instances, compounds of formula (Ib) are isolated as minor isomers along with compounds of formula (Ia) as major isomers, e.g., during column chromatography as described herein.

Compounds of formula (C-1) are compounds of formula (C), as set forth above in Reaction Scheme 1, where $R^1$ is pyrrolidin-1-yl. They can be prepared according to the method described below in relation to Reaction Scheme 2:

REACTION SCHEME 2

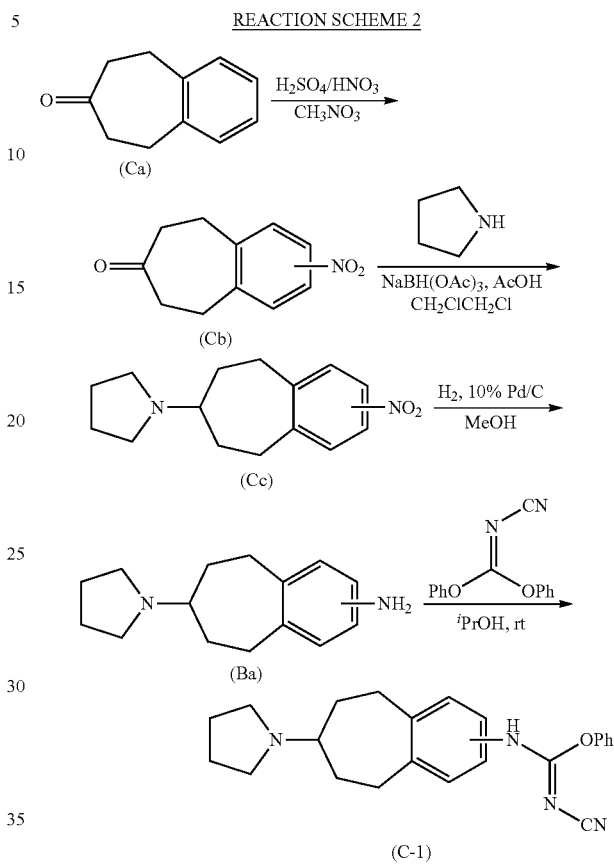

Compounds of formula (Ca) and formula (A) are commercially available or can be prepared according to methods described herein or known to one skilled in the art. Compounds of formula (Ba) are compounds of formula (B), as set forth above in Reaction Scheme 1.

In general, compounds of formula (C-1) are prepared, for example, as set forth above in Reaction Scheme 2, by nitration of the benzo[7]annulene of formula (Ca) to form the nitro compound of formula (Cb). Reductive amination of the keto group in the ketone of formula (Cb) yields the pyrrolidine-substituted compound of formula (Cc). Reduction of the nitro group of the pyrrolidine-substituted compound of formula (Cc), for example, by catalytic hydrogenation, gives the aniline of formula (Ba). Reaction of the aniline of formula (Ba) with diphenyl cyanocarbonimidate of formula (A) yields the compound of formula (C-1). Compounds of formula (C-1) are enantiomeric. The enantiomers of compound (C-1), and similar compounds of the invention, can be isolated, for example, by chiral phase HPLC.

Stereoselective amination of certain cyclic ketones, such as the compounds of formula (Cb) as set forth above, can be very challenging or impossible. Accordingly, one aspect of this invention is directed to a method of using transaminases to produce enantiomerically pure primary amines from cyclic ketones, particularly from cyclic ketones fused to a substituted aromatic ring.

Transaminases (also known as amino transferases) are enzymes that catalyze a transamination reaction between an amino-donor molecule (such as an amine or amino acid) and an amino-acceptor molecule (such as a ketone or an α-keto acid). Specifically, enzymatic transamination involves removing the amino group from the amino-donor molecule (leaving behind a carbonyl group) and transferring the amino group to the amino-acceptor molecule (or α-keto acid) by converting the ketone moiety therein to an amine (or an amino acid). A description of transaminases and their use in stereoselective synthesis can be found in "Transminations. Enzyme Catalysis in Organic Synthesis (2nd Edition) (2002)", by J. David Rozzell and Andreas S. Bommarius, pp. 873-893, which is incorporated in full by reference herein.

Transaminases are particularly suitable for the enzymatic synthesis of chiral amines from the corresponding ketone precursors. Commercially available transaminases can be used to achieve a chiral enzymatic amination of a desired starting material in the preparation of the compounds of the invention. In particular, a ketone of the following formula (i) where n and m are the same and are 0, 1 or 2 and $R^7$ is nitro, halo or $-C(O)OR^2$ (where $R^2$ is as described above in the Summary of the Invention) can be converted under suitable conditions to the corresponding (S)-enantiomer and (R)-enantiomer wherein the carbon to which the amino group is attached is either in the (S) or the (R) configuration, respectively, by utilizing a (S)-specific transaminase and an amino donor molecule, such as L-alanine, or a (R)-specific transaminase and an amino donor molecule, such as L-alanine, as shown below:

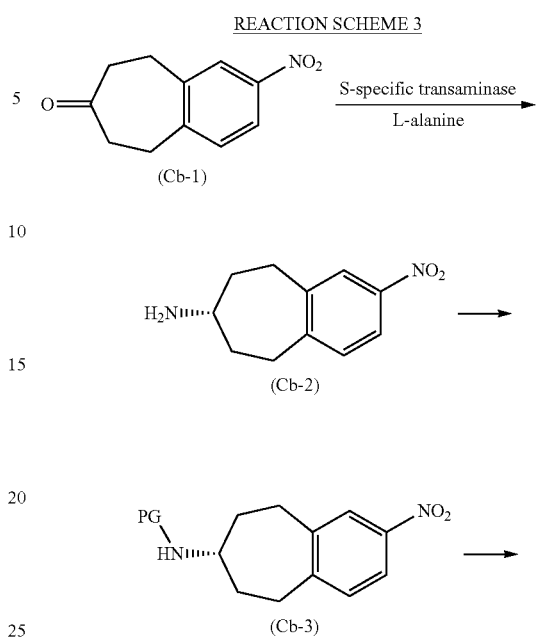

REACTION SCHEME 3

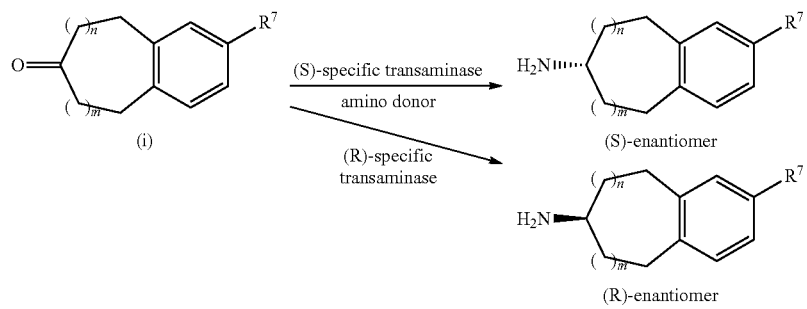

One of ordinary skill in the art would appreciate that the amino group on the (S)-enantiomer and the (R)-enantiomer can be further functionalized by standard procedures known to one skilled in the art. For example, treatment of the above (S)-enantiomer with 1,4-dibromobutane under the appropriate alkylation conditions will result in the amino group being converted to a 1-pyrrolidinyl group. Alternatively, treatment of the above (S)-enantiomer with an appropriate acylating agent with result in the amino group being acylated accordingly, and so forth.

Utilizing the appropriate transaminase to convert the cyclic ketone of formula (i) into the appropriate enantiomer, the appropriate enantiomer can be isolated in greater than 80% ee and preferably greater than 90% ee.

The following Reaction 3, where the compound of formula (Cb-1) is a compound of formula (i) as described above and PG represents a nitrogen protecting group, illustrates a method of preparing a chiral compound of the invention utilizing a transaminase as described above:

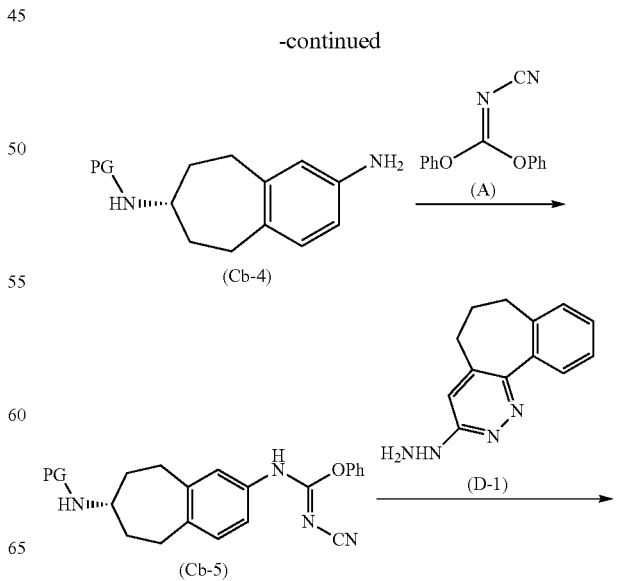

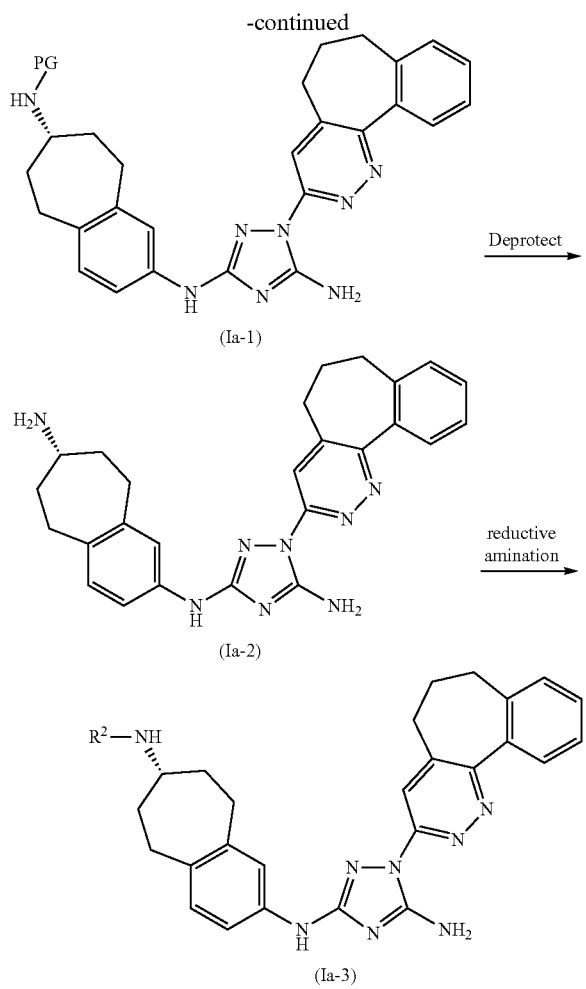

Compounds of formula (Cb-1) are commercially available, or can be prepared by methods known to one skilled in the art. Compounds of formula (D-1) can be prepared according to methods known to one skilled in the art or by methods disclosed herein. The (S)-specific transaminase is commercially available from Codexis. Preferably the (S)-specific transaminase is ATA-103 from Codexis.

In general, compounds of formula (Ia-1) are prepared by the method disclosed above in Reaction Scheme 3 by first converting the ketone of formula (Cb-1) into the chiral compound of formula (Cb-2) wherein the amino group from an amino donor molecule, preferably L-alanine, is transferred to the ketone of formula (Cb-1) through an enzymatic transamination reaction under suitable conditions. In particular, the ketone of formula (Cb-1) is treated with a excess molar amount of an amino donor molecule in the the presence of a catalytic amount of a transaminase, preferably a (S)-specific transaminase, and a stoichiometric or excess stoichiometric amount of a pyruvate reductase mixture that reduces (deactivates) the 2-keto acid side product, thereby driving the reaction into the desired direction. Preferably the pyruvate reductase mixture is PRM-102 from Codexix. The reaction is conducted at ambient temperature, at a pH of between about 7.5 and about 8.0, and for a period of time of between about 24 hours and about 6 days, preferably for about 4 days. The chiral compound of formula (Cb-2) is isolated from the reaction mixture by standard isolation techniques known to one skilled in the art.

Alternatively, the transamination reaction can be driven to completion by coupling the reaction to a second reaction that consumes the 2-keto acid by-product in an essentially irreversible step, as described in more detail in "Transminations. Enzyme Catalysis in Organic Synthesis ($2^{nd}$ Edition) (2002)", by J. David Rozzell and Andreas S. Bommarius, pp. 873-893.

The amino group of the chiral compound of formula (Cb-2) is then protected by standard nitrogen protecting procedures to yield the compound of formula (Cb-3), which is isolated from the reaction mixture by standard isolation techniques known to one skilled in the art. The compound of formula (Cb-3) is then treated to standard reducing conditions, such as treatment with $H_2$/Pd, to produce the corresponding aniline compound of formula (Cb-4), which is isolated from the reaction mixture by standard isolation techniques known to one skilled in the art. The compound of formula (Cb-4) is then treated with diphenyl cyanocarbonimidate of formula (A) to produce the compound of formula (Cb-5), which is isolated from the reaction mixture by standard isolation techniques known to one skilled in the art.

The compound of (Cb-5) is then treated with a compound of formula (D-1) in the presence of an aprotic solvent, preferably toluene, at a temperature of between about 80° C. and about 100° C. for a period of time of between about 12 hours and about 36 hours, preferably for about 24 hours, to yield a compound of formula (Ia-1), which is isolated from the reaction mixture by standard isolation techniques known to one skilled in the art. Compound of formula (Ia-1) is a compound of formula (Ia), as set forth above.

The protecting group on the compound of formula (Ia-1) can be removed under standard deprotecting conditions known to one skilled in the art, such as acid hydrolysis, to produce a compound of formula (Ia-2), which is isolated from the reaction mixture by standard isolation techniques known to one skilled in the art. The compound of formula (Ia-2) can be further treated with the appropriate aldehyde or ketone under standard reductive amination conditions to yield a compound of formula (Ia-3), which is isolated from the reaction mixture by standard isolation techniques known to one skilled in the art.

Compounds of formula (D-1) utilized in Reaction Scheme 3 above are compounds of formula (D), as shown above in Reaction Scheme 1, where A is =C(H)—. Compounds of formula (D-1) can be prepared according to the method disclosed below in Reaction Scheme 4:

REACTION SCHEME 4

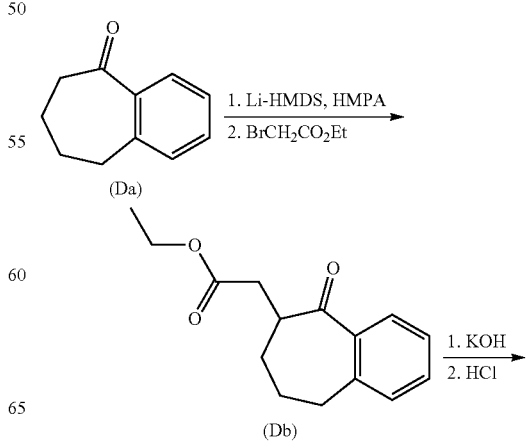

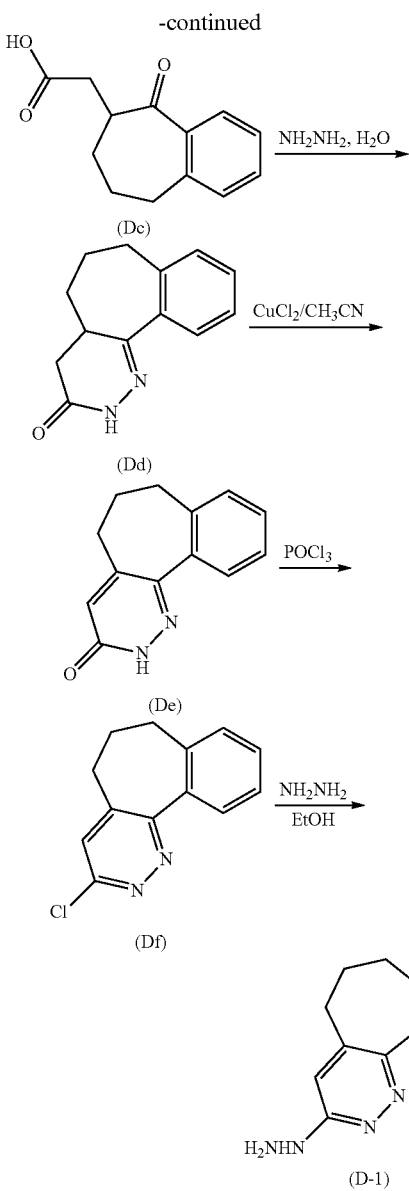

for about 10 minutes, and then allowed to warm to ambient temperature and stirred at ambient temperature for a period of time of between about 30 minutes and 3 hours, preferably for about 2 hours. The compound of formula (Db) is then isolated from the reaction mixture by standard isolation techniques known to one skilled in the art, such as solvent evaporation and purification by flash column chromatography.

The compound of formula (Db) is then treated under basic hydrolysis conditions to form the compound of formula (Dc), which is isolated from the reaction mixture by standard isolation techniques known to one skilled in the art.

The compound of formula (Dc) (1.0 equiv) is then treated with hydrazine hydrate (1.25 equiv) in the presence of a polar protic solvent, such as ethanol, to yield the compound of formula (Dd), which is isolated from the reaction mixture by standard isolation techniques known to one skilled in the art.

A mixture of the compound of formula (Dd) (1.0 equiv) and anhydrous copper(II) chloride (2.0 equiv) is then refluxed in acetonitrile to yield the unsaturated compound of formula (De), which is isolated from the reaction mixture by standard isolation techniques known to one skilled in the art.

A mixture of the compound of formula (De) and phosphoryl chloride, is refluxed for a period of time of between about 1 hour and 3 hours, preferably for about 2 hours to aromatize and chlorinate the ring containing the N—N linkage. After cooling to ambient temperature, the compound of formula (Df) is isolated from the reaction mixture by standard isolation techniques known to one skilled in the art.

A mixture of the compound of formula (Df) (1.0 equiv) and anhydrous hydrazine (19.8 equiv) in a protic solvent, such as ethanol, is refluxed for a period time of between about 4 hours and 24 hours, preferably for about 16 hours. After cooling to ambient temperature, water is added to the mixture and the compound of formula (D-1) is then isolated from the reaction mixture by standard isolation techniques known to one skilled in the art.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

The following specific Synthetic Preparations (for intermediates) and Synthetic Examples (for compounds of the invention) are provided as a guide to assist in the practice of the invention, and are not intended as a limitation on the scope of the invention. The number following each compound below refers to its number in Table 1 and Table 2, as discussed in more detail below.

Compounds of formula (Da) are commercially available or can be prepared by methods known to one skilled in the art or by methods disclosed herein.

In general, compounds of formula (D-1) are prepared, as set forth above in Reaction Scheme 3, by first dissolving the compound of formula (Da) (1.0 equiv) in an anhydrous aprotic polar solvent or mixture of such solvents, for example, tetrahydrofuran with hexamethylphosphoramide (HMPA) (1.2 equiv). The resulting solution is stirred at ambient temperature for about 10 minutes and then cooled to a temperature of between about −10° C. and about 5° C., preferably at 0° C. A strong base, lithium bis(trimethylsilyl)amide (Li-HMDS) (1.1 equiv), is then added dropwise to the stirred mixture over a period of time of between about 20 minutes and 40 minutes, preferably over 30 minutes, while maintaining the temperature of the resulting mixture at between about −10° C. and about 5° C., preferably at 0° C. Ethyl bromoacetate (2.5 equiv) is then added to the resulting anion of (Da) and the resulting mixture is stirred for additional period of time of between about 5 minutes and 15 minutes, preferably Synthetic Preparation 1

Synthesis of 7-oxo-6,7,8,9-tetrahydro-5H-benzo[7]annulene

A Compound of Formula (Ca)

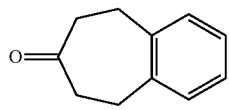

A. Sodium methoxide (9.4 g, 174.2 mmol) was added to a 250 mL of flask with dry methanol (100 mL) at 0° C. After the solid was dissolved, the resulting solution was warmed to ambient temperature and was added to a solution of dimethyl acetone-1,3-dicarboxylate (15.2 g, 87.1 mmol) and o-xylylene dibromide (20 g, 75.7 mmol) in 100 mL of dry THF at 0° C. dropwise within 30 min. After the addition, the reaction mixture was warmed to ambient temperature and stirred overnight. The volatiles were evaporated, the residue was poured into 40 mL of 10% HCl solution and extracted with ethyl acetate (EtOAc) (200 mL×2). The combined extracts were washed with water, saturated NaHCO$_3$ solution and brine. After evaporation, the residual oil was used for next step directly.

B. The crude dimethyl 7-oxo-6,7,8,9-tetrahydro-5H-benzo[7]annulene-6,8-dicarboxylate was dissolved in 200 mL of ethanol (EtOH) and then 100 mL of 2 N KOH. The resulting mixture was refluxed at 85° C. for 17 h. After cooling to ambient temperature, the volatiles were evaporated. To the residue was added 120 mL of 2N HCl at 0° C., the crude product was extracted by EtOAc (200 mL×2). The combined extracts were washed with brine. After being dried (MgSO$_4$), filtered, and concentrated, the residue was purified by flash column chromatography on silica gel (hexanes/EtOAc 8:1) to afford 6.6 g (57%) of 7-oxo-6,7,8,9-tetrahydro-5H-benzo[7]annulene as a white solid: mp 40-41° C.; $^1$H NMR (300 MHz, CDCl$_3$) δ: 7.21 (m, 4H), 2.94-2.90 (m, 4H), 2.63-2.60 (m, 4H); LC-MS: 161 (M+H)$^+$.

Synthetic Preparation 2

Synthesis of 2-nitro-8,9-dihydro-5H-benzo[7]annulene-7(6H)-one

A Compound of Formula (Cb)

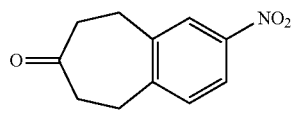 [SMILES: O=C1CCc2ccc([N+](=O)[O-])cc2CC1]

To a solution of cold (0° C.) concentrated sulfuric acid (15 mL) was added 70% nitric acid (15 mL) dropwise over 30 min. The addition was controlled to maintain the internal reaction temperature below 5° C. After the addition, the resulting solution was transferred into an addition funnel and was added dropwise to a solution of 7-oxo-6,7,8,9-tetrahydro-5H-benzo[7]annulene (14 g, 87.5 mmol) in nitromethane (80 mL) at 0° C. over a period of 40 min. After the addition, the reaction mixture was stirred at 0° C. for 2 h. Then ice water (~80 mL) was added to the reaction mixture, and the mixture was stirred for additional 30 min. Then the mixture was transferred to a separatory funnel where the layers were separated. The aqueous layer was extracted with ethyl acetate (3×80 mL). The combined layers were washed with cold water, sat. NaHCO$_3$ solution and brine. After being dried (MgSO$_4$), filtered, and concentrated, the residue was purified by flash column chromatography on silica gel (hexanes/EtOAc=3:1 to 2:1) to afford the mixture of nitro regioisomers (~15 g), which was then purified by recrystallization from MTBE (tert-butyl methyl ether, 180 mL) to yield 7.3 g of 2-nitro-8,9-dihydro-5H-benzo[7]annulene-7(6H)-one (40% yield) as a yellow solid: $^1$H NMR (300 MHz, CDCl$_3$) δ: 8.10-8.06 (m, 2H), 7.40-7.37 (m, 1H), 3.04-3.00 (m, 4H), 2.67-2.65 (m, 4H); LC-MS: 206 (M+H)$^+$.

Synthetic Preparation 3

Synthesis of 1-(2-nitro-6,7,8,9-tetrahydro-5H-benzo[7]annulene-7-yl)pyrrolidine

A Compound of Formula (Cc)

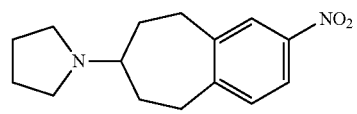 [SMILES: Nc1ccc2c(c1)CCC(N1CCCC1)CC2]

Pyrrolidine (0.85 g, 12 mmol) and 2-nitro-7-oxo-6,7,8,9-tetrahydro-5H-benzo[7]annulene (2.05 g, 10 mmol) were mixed in 1,2-dichloroethane (35 mL) and then treated with NaBH(OAc)$_3$ (3.18 g, 15 mmol) and AcOH (0.60 g, 10 mmol). The mixture was stirred at ambient temperature under a N$_2$ atmosphere overnight. The reaction mixture was quenched with saturated NaHCO$_3$, and the product was extracted with EtOAc (3×30 mL). The organic layers were combined and dried over NaSO$_4$. The solvent was evaporated and the residue was purified by flash column chromatography eluting with CH$_2$Cl$_2$/DMA=1/1 (DMA=CH$_2$Cl$_2$/MeOH/30% NH$_3$=80/19/1) to afford 1-(2-nitro-6,7,8,9-tetrahydro-5H-benzo[7]annulene-7-yl)pyrrolidine, a yellow oil (2.2 g, 85%); MS (m/e): 261 (M+H$^+$).

Synthetic Preparation 4

Synthesis of 1-(2-amino-6,7,8,9-tetrahydro-5H-benzo[7]annulene-7-yl)pyrrolidine

A Compound of Formula (Ba)

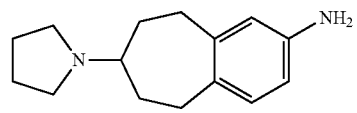

A mixture of 1-(2-nitro-6,7,8,9-tetrahydro-5H-benzo[7]annulene-7-yl)pyrrolidine (2.0 g; 7.69 mmol) and 10% palladium on carbon (0.2 g, ~50% water) in methanol (150 mL) was shaken under hydrogen (40 psi) for 1 h. After this time the reaction mixture was filtered through diatomaceous earth and the filtrate was concentrated under reduced pressure to afford 1-(2-amino-6,7,8,9-tetrahydro-5H-benzo[7]annulene-7-yl)pyrrolidine as an oil (quantitative yield); MS (m/e): 231 (M+H$^+$).

Synthetic Preparation 5

Synthesis of Phenyl N'-cyano-N-(7-(pyrrolidin-1-yl)-6,7,8,9-tetrahydro-5H-benzo[7]annulene-2-yl)carbamimidate A Compound of Formula (C-1)

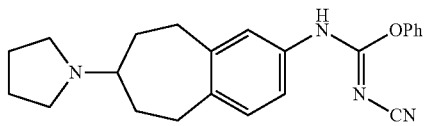 [SMILES: N#C/N=C(/Nc1ccc2c(c1)CCC(N1CCCC1)CC2)Oc1ccccc1]

A mixture of 1-(2-amino-6,7,8,9-tetrahydro-5H-benzo[7]annulene-7-yl)pyrrolidine (1.7 g; 7.39 mmo) and diphenyl cyanocarboimidate (1.76 g, 7.39 mmol) in 20 mL of isopropanol was stirred at ambient temperature overnight. The solid was filtered, washed with isopropanol and ether and dried to give phenyl N'-cyano-N-(7-(pyrrolidin-1-yl)-6,7,8,9-tetrahydro-5H-benzo[7]annulene-2-yl)carbamimidate, as a white solid (2.2 g, 80%). MS (m/e): 375 (M+H$^+$).

Synthetic Preparation 6

Isolation of Phenyl (S)—N'-cyano-N-(7-(pyrrolidin-1-yl)-6,7,8,9-tetrahydro-5H-benzo[7]annulene-2-yl)carbamimidate and Phenyl (R)—N'-cyano-N-(7-(pyrrolidin-1-yl)-6,7,8,9-tetrahydro-5H-benzo[7]annulene-2-yl)carbamimidate Enantiomers of the Compound of Formula (C-1)

Phenyl N'-cyano-N-(7-(pyrrolidin-1-yl)-6,7,8,9-tetrahydro-5H-benzo[7]annulene-2-yl)carbamimidate (0.43 g, racemic) was eluted on a chiral column chromatography mobile phase; ethanol/MeOH/triethyl amine=1/1/0.2% to afford phenyl (S)—N'-cyano-N-(7-(pyrrolidin-1-yl)-6,7,8,9-tetrahydro-5H-benzo[7]annulene-2-yl)carbamimidate and phenyl (R)—N'-cyano-N-(7-(pyrrolidin-1-yl)-6,7,8,9-tetrahydro-5H-benzo[7]annulene-2-yl)carbamimidate: Chiral column: Chiralcel OJ, 21.2×250 mm. 10 µM; packing material: cellulose tris-(4-methylbenzoate) coated on 10 µm silica gel substrate. Flow rate 9.9 mL/min, sample solubility 30 mg/mL in methanol. Single enantiomers were isolated in 170 mg and 190 mg quantities, respectively. Absolute configuration of each enantiomer was not determined at this time.

Synthetic Preparation 7

Synthesis of ethyl 2-(5-oxo-6,7,8,9-tetrahydro-5H-benzo[7]annulene-6-yl)acetate

Compound of Formula (Db)

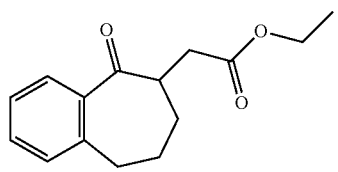 [SMILES: CCOC(=O)CC1CCCc2ccccc2C1=O]

To a mixture of 1-benzosuberone (5.0 g, 31.2 mmol, Aldrich) in dry tetrahydrofuran (THF) (20 mL) was added hexamethylphosphoramide (6.5 mL, 37.5 mmol) (99%, Aldrich). The resulting mixture was stirred at ambient temperature for 10 min and then cooled to 0° C. with a ice-water bath, 1.0 M solution of lithium bis(trimethylsilyl)-amide in THF (32.7 mL, 32.7 mmol) was added dropwise in 30 min. After the addition, the reaction mixture was stirred at 0° C. for 30 min. Ethyl bromoacetate (8.7 mL, 78.1 mmol) was then added. After stirring for a further 10 min, the reaction mixture was warmed to ambient temperature and stirred for 2 h. Solvent was evaporated, the residue was diluted with ethyl acetate (EtOAc) (300 mL), and washed with water and brine. After being dried (MgSO$_4$), filtered, and concentrated, the residue was purified by flash column chromatography eluting with hexanes-ethyl acetate 6:1→4:1) to afford 6.6 g of the compound of formula (Db), ethyl 2-(5-oxo-6,7,8,9-tetrahydro-5H-benzo[7]annulene-6-yl)acetate, as an orange oil (84%), $^1$H NMR (300 MHz, CDCl$_3$) δ: 7.69-7.21 (m, 4H), 4.22-4.05 (m, 2H), 3.40-3.30 (m, 1H), 3.12-2.92 (m, 3H), 2.52-2.43 (m, 1H), 2.20-1.58 (m, 4H), 1.28-1.21 (m, 3H); LC-MS: purity: 91.8%; MS (m/e): 247 (MH$^+$).

Synthetic Preparation 8

Synthesis of 2-(5-oxo-6,7,8,9-tetrahydro-5H-benzo[7]annulene-6-yl)acetic acid

Compound of Formula (Dc)

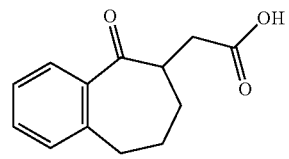 [SMILES: O=C(O)CC1CCCc2ccccc2C1=O]

The compound of formula (Db), ethyl 2-(5-oxo-6,7,8,9-tetrahydro-5H-benzo[7]annulene-6-yl)acetate, (6.6 g, 26.8 mmol) was dissolved in ethanol (EtOH) (30 mL), then 10% potassium hydroxide (KOH) aqueous solution (37.5 mL, 67 mmol) was added and the resulting mixture was refluxed for 2 h. After cooling to ambient temperature, the EtOH was removed by evaporation. The residue was extracted with EtOAc twice (15 mL×2). The aqueous layer was then transferred into a flask and cooled with an ice-water bath, con. HCl was added dropwise to adjust pH to about 2.0. EtOAc (60 mL) was then added, the layers were separated, and the aqueous layer was extracted with EtOAc. The combined extracts were washed with brine. After being dried (MgSO$_4$), filtered, and concentrated, the compound of formula (Dc), 2-(5-oxo-6,7,8,9-tetrahydro-5H-benzo[7]annulene-6-yl)acetic acid, was obtained as an orange oil (5.7 g, 97%); $^1$H NMR (300 MHz, CDCl$_3$) δ: 7.71-7.68 (m, 1H), 7.41-7.20 (m, 3H), 3.37-3.31 (m, 1H), 3.12-2.91 (m, 3H), 2.57-2.49 (m, 1H), 2.15-1.90 (m, 2H), 1.75-1.62 (m, 2H); LC-MS: purity: 100%; MS (m/e): 219 (MH$^+$).

Synthetic Preparation 9

Synthesis of 4a,5,6,7-tetrahydro-2H-benzo[6,7]cyclohepta[c]pyridazin-3(4H)-one

Compound of Formula (Dd)

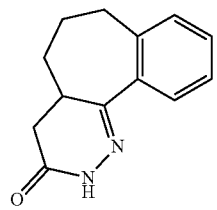 [SMILES: O=C1CC2CCCc3ccccc3C2=NN1]

A. A mixture of the compound of formula (Dc), 2-(5-oxo-6,7,8,9-tetrahydro-5H-benzo[7]annulene-6-yl)acetic acid, (5.7 g, 26.1 mmol) and hydrazine hydrate (1.6 mL, 32.7 mmol) in 20 mL of ethanol was refluxed for 2 h, cooled and filtered (washed with small amount of EtOH) to give the compound of formula (Dd), 4a,5,6,7-tetrahydro-2H-benzo[6,7]cyclohepta[c]pyridazin-3(4H)-one, as a white solid (4.7 g, 84%); $^1$H NMR (300 MHz, CDCl$_3$) δ: 8.61 (bs, 1H), 7.53-7.14 (m, 4H), 2.98-2.75 (m, 3H), 2.58 (dd, J=15.3, 16.8 Hz, 1H), 2.31 (dd, J=12.0, 16.8 Hz, 1H), 1.96-1.59 (m, 4H); LC-MS: purity: 100%; MS (m/e): 215 (MH$^+$).

B. Alternatively, a mixture of benzosuberone (10.6 g, 66.2 mmol), glyoxylic acid monohydrate (6.08 g, 66.2 mmol), sodium hydroxide (10.6 g, 265 mmol), ethanol (40 mL) and water (100 mL) were stirred overnight at ambient temperature, and then heated under reflux for 1 h. The mixture was cooled, then diluted with water and extracted twice with dichloromethane (subsequently discarded). The aqueous layer was then acidified with 10% aqueous hydrochloric acid. Ice was added for cooling. The mixture was then filtered to give a pale yellow solid, 10.5 g (after air drying). The crude solid was then heated at 100° C. for 1 h with a mixture of acetic acid (60 mL), water (30 mL) and zinc dust (6 g). The reaction mixture was cooled to ambient temperature and filtered. The filtrate was extracted with ethyl acetate. The organic layer was washed three times with saturated sodium chloride solution, then dried over anhydrous sodium sulfate and concentrated under vacuum. The crude residue was heated with ethanol (25 mL) and hydrazine monohydrate (10 mL) under reflux for 3 h. The solvent was removed under vacuum and the residue was crystallized from benzene/ethanol, 1/1, to give 4a,5,6,7-tetrahydro-2H-benzo[6,7]cyclohepta[c]pyridazin-3(4H)-one as a white solid, 2.31 g; $^1$H NMR (CDCl$_3$, 300 MHz) 8.66 (s, 1H), 7.52 (d, 1H), 7.24-7.50 (m, 2H), 7.16 (d, 2H), 2.75-3.00 (m, 3H), 2.56 (dd, 1H), 2.31 (dd, 1H), 1.60-1.90 (m, 4H) ppm; MS (ES) 215 (M+H). This procedure followed that reported by V. Peesapati and S. C. Venkata, *Indian J. Chem.*, 41B, 839 (2002).

Synthetic Preparation 10

Synthesis of 6,7-dihydro-2H-benzo[6,7]cyclohepta[1,2-c]pyridazin-3(5H)-one

Compound of Formula (De)

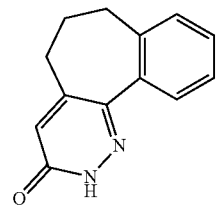 [SMILES: O=c1cc2c(n[nH]1)-c1ccccc1CCC2]

A. A mixture of the compound of formula (Dd), 4a,5,6,7-tetrahydro-2H-benzo[6,7]cyclohepta[c]pyridazin-3(4H)-one (4.7 g, 22 mmol) and anhydrous copper(II) chloride (6 g, 44 mmol) was refluxed in acetonitrile (45 mL) for 2 hours. After cooling to ambient temperature, the mixture was poured into ice-water (200 g) and the solid obtained was washed with 10% HCl solution twice (about 20 mL×2) and cold water twice (about 20 mL×2). After freeze-drying, the compound of formula (De), 6,7-dihydro-2H-benzo[6,7]cyclohepta[1,2-c]pyridazin-3(5H)-one (4.2 g, 90%) was obtained as a white solid, $^1$H NMR (300 MHz, CDCl$_3$) δ: 10.80 (bs, 1H), 7.53-7.21 (m, 4H), 6.77 (s, 1H), 2.66 (t, J=6.9 Hz, 2H), 2.45 (t, J=6.9 Hz, 2H), 2.14 (quant, J=6.9 Hz, 2H); LC-MS: purity: 100%; MS (m/e): 213 (MH$^+$).

B. Alternatively, a solution of 4a,5,6,7-tetrahydro-2H-benzo[6,7]cyclohepta[c]pyridazin-3(4H)-one (2.31 g, 10.74 mmol), sodium m-nitrobenzenesulfonate (2.48 g, 11 mmol), sodium hydroxide (1.86 g, 46.5 mmol) in water (80 mL) was heated under reflux for 1.5 h. The solution was cooled to ambient temperature, and then acidified with concentrated hydrochloric acid. The solid which precipitated was filtered off, washed with water and crystallized from ethanol to give 6,7-dihydro-2H-benzo[6,7]cyclohepta[1,2-c]pyridazin-3(5H)-one as tan crystals, 1.46 g; $^1$H NMR (DMSO-d$_6$, 300 MHz) 13.04 (s, 1H), 7.25-7.45 (m, 4H), 6.78 (s, 1H), 2.49 (m, 2H), 2.35 (m, 2H), 2.04 (m, 2H) ppm; MS (ES) 213 (M+H).

Synthetic Preparation 11

Synthesis of 3-chloro-6,7-dihydro-5H-benzo[6,7]cyclohepta[1,2-c]pyridazine

Compound of Formula (Df)

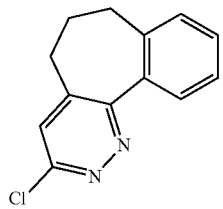 [SMILES: Clc1cc2c(nn1)-c1ccccc1CCC2]

A. A mixture of the compound of formula (De), 6,7-dihydro-2H-benzo[6,7]cyclohepta[1,2-c]pyridazin-3(5H)-one (4.0 g, 19.3 mmol) and POCl$_3$ (20 mL) was refluxed for 2 h. After cooling to ambient temperature, the volatiles were evaporated. The residue was poured into a mixture of ice water and sodium bicarbonate, $CH_2Cl_2$ (200 mL) was added to dissolve the solid. The layers were separated, and the aqueous layer was extracted with $CH_2Cl_2$ one more time. The combined organic layers were washed with brine. After being dried ($MgSO_4$), filtered, and concentrated, the compound of formula (Df), 3-chloro-6,7-dihydro-5H-benzo[6,7]cyclohepta[1,2-c]pyridazine was obtained as a yellow solid (4.3 g, 99%), $^1$H NMR (300 MHz, $CDCl_3$) δ: 7.82 (m, 1H), 7.45-7.24 (m, 4H), 2.59-2.51 (m, 4H), 2.27 (quant, J=6.9 Hz, 2H); LC-MS: purity: 100%; MS (m/e): 231 ($MH^+$).

B. Alternatively, 6,7-dihydro-2H-benzo[6,7]cyclohepta[1,2-c]pyridazin-3(5H)-one was heated with 20 mL of phosphorus (III) oxychloride at 100° C. for 4.75 h. The solvent was removed under vacuum. The residue was treated with ice and saturated sodium bicarbonate solution. The solid which formed was filtered off, washed well with water and air-dried to yield the corresponding 3-chloro-6,7-dihydro-5H-benzo[6,7]cyclohepta[1,2-c]pyridazine (1.6 g); $^1$H NMR ($CDCl_3$, 300 MHz) 7.82 (m, 1H), 7.44 (m, 2H), 7.39 (s, 1H), 7.27 (m, 1H), 2.55 (m, 4H), 2.32 (m, 2H) ppm; MS (ES) 231/233 (M+H).

Synthetic Preparation 12

Synthesis of 3-hydrazino-6,7-dihydro-5H-benzo[6,7]cyclohepta[1,2-c]pyridazine

Compound of Formula (D-1)

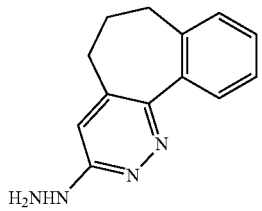

A. A mixture of the compound of formula (Df), 3-chloro-6,7-dihydro-5H-benzo[6,7]cyclohepta[1,2-c]pyridazine, (4.3 g, 18.6 mmol) and anhydrous hydrazine (11.7 mL, 370 mmol) in 45 mL of ethanol was refluxed for 16 h. After cooling to ambient temperature, 5 mL of water was added and the volatiles were then evaporated. To the solid residue was added cold water (about 80 mL). After sonication for 10 min, the resulting solid was collected by filtration and washed with cold water three times. After freeze-drying, the compound of formula (D-1), 3-hydrazino-6,7-dihydro-5H-benzo[6,7]cyclohepta[1,2-c]pyridazine, (4.14 g, 98%) was obtained as a slight yellow solid, $^1$H NMR (300 MHz, $CD_3OD$) δ: 7.59 (m, 1H), 7.39-7.26 (m, 3H), 7.04 (s, 1H), 2.54 (t, J=6.9 Hz, 2H), 2.47 (t, J=6.9 Hz, 2H), 2.18 (quant, J=6.9 Hz, 2H); LC-MS: purity: 100%; MS (m/e): 227 ($MH^+$).

B. Alternatively, 3-chloro-6,7-dihydro-5H-benzo[6,7]cyclohepta[1,2-c]pyridazine (1.6 g) was heated with anhydrous hydrazine (4 mL) in ethanol (50 mL) at 100° C. for 4.75 h. The solvent was removed under vacuum. The residue was partitioned between chloroform and 1M saturated aqueous potassium carbonate. The organic layer was dried over anhydrous sodium sulfate and concentrated under vacuum to give 3-hydrazino-6,7-dihydro-5H-benzo[6,7]cyclohepta[1,2-c]pyridazine as a brown solid; $^1$H NMR ($CDCl_3$, 300 MHz) 7.74 (m, 1H), 7.30 (m, 2H), 7.17 (m, 1H), 6.92 (s, 1H), 2.49 (m, 2H), 2.39 (m, 2H), 2.12 (m, 2H) ppm; MS (ES) 227 (M+H).

Synthetic Preparation 13

Synthesis of Phenyl N'-cyano-N-(7-(t-butoxycarbonylamino)-6,7,8,9-tetrahydro-5H-benzo[7]annulene-2-yl)carbamimidate (Cb-5)

Finely ground 2-Nitro-8,9-dihydro-5H-benzo[7]annulen-7(6H)-one(8.00 g, 39.0 mmol) and L-alanine (34.7 g, 390 mmol) were added to the reaction buffer (1000 mL, Codexis/BioCatalytics). The mixture was stirred vigorously for about 20 min in order to obtain a uniform suspension (bright-yellow in color). The pyruvate reductase mix (40.0 g, PRM-102, Codexis/BioCatalytics) and the transaminase (0.85 g, ~10.6 wt %, ATA-103) were added. The pH of the reaction mixture was ~7. Stirring was continued at a slow pace; the pH was checked once a day and, if necessary, adjusted to pH 7.0-7.5 using 1M NaOH. During the course of the reaction the color of the mixture changed to a yellow-orange color. After 6 days HPLC analysis showed 99% conversion. The reaction was worked up by adding sat. $NaHCO_3$ solution (200 mL) and $CHCl_3$ (600 mL). This mixture was stirred vigorously to ensure complete transfer of the product into the organic phase. After stirring overnight two layers had formed and the organic layer contained large amounts of a gel-like solid. The organic layer was separated and filtered through a large glass frit (medium) to remove the gel-like solid. The aqueous phase was extracted three times with DCM. The combined organic layers were filtered through $MgSO_4$ and the solvents were evaporated to give the desired amine, (7S)-2-nitro-7-amino-7,8,9-trihydro-5H-benzo[7]annulene (7.27 g, 91%, dark-red oil).

The single enantiomer was then BOC-protected, the nitro group reduced by treatment with $H_2$/Pd and the primary aniline treated with diphenyl cyanocarboimidate (slight excess) in 20 mL of isopropanol with stirring at ambient temperature overnight. The solid was filtered, washed with isopropanol and ether and dried to give phenyl (7S) N'-cyano-N-(7-amino-6,7,8,9-tetrahydro-5H-benzo[7]annulene-2-yl)carbamimidate, as a white solid in high yield (from the single enantiomer via transamination).

Synthetic Example 1

Synthesis of 1-(6,7-dihydro-5H-benzo[6,7]cyclohepta[1,2-c]pyridazin-3-yl)-$N^3$-((7S)-7-(t-butoxycarbonylamino)-6,7,8,9-tetrahydro-5H-benzo[7]annulene-2-yl)-1H-1,2,4-triazole-3,5-diamine

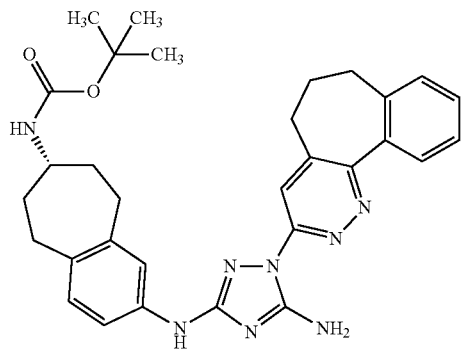 [SMILES: CC(C)(C)OC(=O)N[C@H]1CCc2ccc(Nc3nc(N)n(-c4cc5c(nn4)-c4ccccc4CCC5)n3)cc2CC1]

Phenyl N'-cyano-N-(7-(t-butoxycarbonylamino)-6,7,8,9-tetrahydro-5H-benzo[7]annulene-2-yl)carbamimidate (2.00 g, 4.75 mmol) and 3-hydrazino-6,7-dihydro-5H-benzo[6,7]cyclohepta[1,2-c]pyridazine (1.08 g, 4.75 mmol) were mixed in dry toluene (40 ml). The suspension was heated to 90° C. and stirred for 24 h. The clear solution was allowed to cool to ambient temperature and the toluene was evaporated using a rotavapor. The crude product was then checked by HPLC and TLC. Column chromatography on silica gel using $CHCl_3$ and 5% $NH_3$ (2M in MeOH) afforded some clean fractions of product which gave 367 mg (14%) of the desired product, 1-(6,7-dihydro-5H-benzo[6,7]cyclohepta[1,2-c]pyridazin-3-yl)-$N^3$-((7S)-7-(t-butoxycarbonylamino)-6,7,8,9-tetrahydro-5H-benzo[7]annulen-2-yl)-1H-1,2,4-triazole-3,5-diamine. The impure fractions were further purified by reverse phase HPLC to yield another 515 mg (20%) of the desired product, compound #13, $^1$H NMR (DMSO-$d_6$, 300 MHz) 9.04 (s, 1H, NH), 7.92 (s, 1H), 7.86 (s, 2H), 7.69 (m, 1H), 7.43 (m, 3H), 7.34 (m, 1H), 7.23 (m, 1H), 6.96 (d, 1H), 6.83 (d, 1H), 3.49 (m, 1H), 2.72-2.39 (m, 8H), 2.22 (m, 2H), 2.07 (s, 1H), 1.92 (m, 2H), 1.38 (s, 9H), 1.17 (m, 2H) ppm; trifluoroacetic acid salt MS (ES) 553.24 (M+H), 551.42 (M−H).

Synthetic Example 2

The following compounds of the invention were prepared according to the methods similar to those described herein:

1-(6,7-dihydro-5H-benzo[6,7]cyclohepta[1,2-c]pyridazin-3-yl)-$N^3$-(7-(acetamido)-6,7,8,9-tetrahydro-5H-benzo[7]annulen-2-yl)-1H-1,2,4-triazole-3,5-diamine, compound #1, $^1$H-NMR (DMSO-$d_6$, 300 MHz) 9.07 (s, 1H), 7.93 (s, 1H), 7.90-7.65 (m, 3H), 7.47-7.31 (m, 3H), 7.24 (s, 1H), 7.00 (d, 1H), 3.89-3.80 (m, 1H), 2.71-2.50 (m, 8H), 2.30-2.19 (m, 2H), 1.96-1.88 (m, 2H), 1.80 (s, 3H), 1.37-1.19 (m, 2H) ppm; MS (ES) 495.21 (M+H);

1-(6,7-dihydro-5H-benzo[6,7]cyclohepta[1,2-c]pyridazin-3-yl)-$N^3$-(7-((2R)-2-(methoxycarbonyl)pyrrolidin-1-yl)-6,7,8,9-tetrahydro-5H-benzo[7]annulen-2-yl)-1H-1,2,4-triazole-3,5-diamine, compound #2, $^1$H-NMR (CDCl$_3$, 300 MHz) 8.90-8.78 (m, 1H), 8.48 (bs, 2H), 7.93 (s, 1H), 7.80-7.78 (m, 1H), 7.47-7.41 (m, 2H), 7.38-7.30 (m, 3H), 7.05-7.00 (m, 1H), 3.82 (s, 3H), 3.80-3.64 (m, 2H), 2.94-2.81 (m, 3H), 2.79-2.71 (m, 4H), 2.70-2.67 (m, 3H), 2.38-2.43 (m, 4H), 2.38-2.29 (m, 3H), 1.80-1.60 (m, 2H) ppm; MS (ES) 565.29 (M+H);

1-(6,7-dihydro-5H-benzo[6,7]cyclohepta[1,2-c]pyridazin-3-yl)-$N^3$-(7-(4,4-difluoropiperidin-1-yl)-6,7,8,9-tetrahydro-5H-benzo[7]annulen-2-yl)-1H-1,2,4-triazole-3,5-diamine, compound #3, $^1$H-NMR (DMSO-$d_6$, 300 MHz) 9.60 (s, 1H), 9.11 (s, 1H), 7.92 (s, 1H), 7.85 (s, 1H), 7.71-7.68 (m, 1H), 7.51-7.45 (m, 2H), 7.39-7.33 (m, 2H), 7.08 (d, 1H), 3.67 (t, 1H), 3.52 (d, 2H), 3.18 (bs, 2H), 2.84-2.52 (m, 6H), 2.37-2.22 (m, 8H), 1.58-1.41 (m, 3H) ppm; MS (ES) 557.23 (M+H);

1-(6,7-dihydro-5H-benzo[6,7]cyclohepta[1,2-c]pyridazin-3-yl)-$N^3$-(7-((methoxycarbonylmethyl)(methyl)amino)-6,7,8,9-tetrahydro-5H-benzo[7]annulen-2-yl)-1H-1,2,4-triazole-3,5-diamine, compound #4, $^1$H-NMR (DMSO-$d_6$, 300 MHz) 9.62 (s, 1H), 9.11 (s, 1H), 7.92 (s, 1H), 7.81 (s, 1H), 7.78-7.71 (m, 1H), 7.45-7.41 (m, 2H), 7.38-7.32 (m, 1H), 7.04 (d, 1H), 4.37 (d, 1H), 4.11 (d, 1H), 3.78 (s, 2H), 3.59 (t, 1H), 2.81-2.74 (m, 4H), 2.65-2.57 (m, 7H), 2.31-2.21 (m, 3H), 1.59-1.40 (m, 2H) ppm; MS (ES) 539.21 (M+H);

1-(6,7-dihydro-5H-benzo[6,7]cyclohepta[1,2-c]pyridazin-3-yl)-$N^3$-(7-((2R)-2-(carboxy)pyrrolidin-1-yl)-6,7,8,9-tetrahydro-5H-benzo[7]annulen-2-yl)-1H-1,2,4-triazole-3,5-diamine, compound #5, $^1$H-NMR (DMSO-$d_6$, 300 MHz) 9.55 (s, 1H), 9.18 (s, 1H), 7.94 (s, 1H), 7.72-7.68 (m, 1H), 7.47-7.40 (m, 2H), 7.38-7.31 (m, 2H), 7.05 (d, 1H), 5.05-4.70 (bs, 3H), 4.55 (q, 1H), 3.64 (t, 1H), 3.52-3.48 (m, 1H), 3.31-3.25 (m, 1H), 2.80-2.70 (m, 3H), 2.62-2.52 (m, 3H), 2.39-2.20 (m, 5H), 2.09-1.78 (m, 4H), 1.49-1.38 (m, 3H) ppm; MS (ES) 551.27 (M+H);

1-(6,7-dihydro-5H-benzo[6,7]cyclohepta[1,2-c]pyridazin-3-yl)-$N^3$-(7-(4-(ethoxycarbonyl)piperidin-1-yl)-6,7,8,9-tetrahydro-5H-benzo[7]annulen-2-yl)-1H-1,2,4-triazole-3,5-diamine, compound #6, $^1$H-NMR (DMSO-$d_6$, 300 MHz) 9.11 (s, 1H), 8.97-8.90 (m, 1H), 7.94 (s, 1H), 7.85 (s, 1H), 7.71-7.68 (m, 1H), 7.50-7.40 (m, 2H), 7.38-7.30 (m, 2H), 7.05 (d, 1H), 4.09 (q, 2H), 3.55 (t, 1H), 3.38 (d, 1H), 3.10 (q, 1H), 2.85-2.57 (m, 5H), 2.52-2.42 (m, 6H), 2.29-2.18 (m, 3H), 2.06 (d, 2H), 1.77-1.70 (m, 2H), 1.54-1.36 (m, 3H), 1.29 (t, 3H) ppm; MS (ES) 593.28 (M+H);

1-(6,7-dihydro-5H-benzo[6,7]cyclohepta[1,2-c]pyridazin-3-yl)-$N^3$-(7-(4-(carboxy)piperidin-1-yl)-6,7,8,9-tetrahydro-5H-benzo[7]annulen-2-yl)-1H-1,2,4-triazole-3,5-diamine, compound #7, $^1$H-NMR (DMSO-$d_6$, 300 MHz) 9.90 (bs, 1H), 9.10 (s, 1H), 7.96 (s, 2H), 7.74-7.69 (m, 1H), 7.50-7.41 (m, 2H), 7.37-7.40 (m, 1H), 7.05 (d, 1H), 4.40-3.83 (m, 5H), 3.53-3.44 (m, 1H), 3.36 (d, 1H), 3.12-2.98 (m, 1H), 2.83-2.71 (m, 2H), 2.62-2.59 (m, 1H), 2.57-2.43 (m, 7H), 2.41-2.36 (m, 1H), 2.29-2.20 (m, 1H), 2.02-1.91 (m, 2H), 1.50-1.38 (m, 1H) ppm; MS (ES) 565.26 (M+H);

1-(6,7-dihydro-5H-benzo[6,7]cyclohepta[1,2-c]pyridazin-3-yl)-$N^3$-(7-((carboxymethyl)(methyl)amino)-6,7,8,9-tetrahydro-5H-benzo[7]annulen-2-yl)-1H-1,2,4-triazole-3,5-diamine, compound #8, $^1$H-NMR (DMSO-$d_6$, 300 MHz) 9.42 (s, 1H), 9.10 (s, 1H), 7.95 (s, 1H), 7.87 (s, 1H), 7.73-7.68 (m, 1H), 7.48-7.41 (m, 2H), 7.39-7.33 (m, 2H), 7.05 (d, 1H), 4.10 (bs, 3H), 3.57 (t, 1H), 2.78 (s, 3H), 2.68-2.45 (m, 9H), 2.3.4-2.22 (m, 3H). 1.55-1.39 (m, 2H) ppm; MS (ES) 525.22 (M+H);

1-(6,7-dihydro-5H-benzo[6,7]cyclohepta[1,2-c]pyridazin-3-yl)-$N^3$-(7-(4-ethoxycarbonylmethyl)piperazin-1-yl)-6,7,8,9-tetrahydro-5H-benzo[7]annulen-2-yl)-1H-1,2,4-triazole-3,5-diamine, compound #9, $^1$H-NMR (DMSO-$d_6$, 300 MHz) 9.21 (s, 1H), 9.12 (s, 1H), 7.93 (s, 1H), 7.87 (s, 1H), 7.73-7.69 (m, 1H), 7.49-7.41 (m, 3H), 7.38-7.32 (m, 2H), 7.06 (d, 1H), 4.11 (q, 2H), 3.54-3.29 (m, 5H), 3.13-2.97 (m, 4H), 2.80-2.70 (m, 8H), 2.60 (t, 2H), 2.37-2.22 (m, 4H), 1.53-1.39 (m, 2H), 1.26 (t, 3H) ppm; MS (ES) 608.31 (M+H);

1-(6,7-dihydro-5H-benzo[6,7]cyclohepta[1,2-c]pyridazin-3-yl)-$N^3$-(7-(4-(carboxymethyl)piperazin-1-yl)-6,7,8,9-tetrahydro-5H-benzo[7]annulen-2-yl)-1H-1,2,4-triazole-3,5-diamine, compound #10, MS (ES) 580.25 (M+H);

1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulen-1-yl)-1H-1,2,4-triazole-3,5-diamine, compound #11, MS (ES) 507.24 (M+H), 505.33 (M−H);

1-(6,7-dihydro-5H-benzo[6,7]cyclohepta[1,2-c]pyridazin-3-yl)-$N^5$-(7-(pyrrolidin-1-yl)-6,7,8,9-tetrahydro-5H-benzo[7]annulen-1-yl)-1H-1,2,4-triazole-3,5-diamine, compound #12, MS (ES) 507.25 (M+H), 505.28 (M−H);

1-(6,7-dihydro-5H-benzo[6,7]cyclohepta[1,2-c]pyridazin-3-yl)-$N^5$-((7S)-7-(t-butoxycarbonylamino)-6,7,8,9-tetrahydro-5H-benzo[7]annulen-2-yl)-1H-1,2,4-triazole-3,5-diamine, compound #14, MS (ES) 553.31 (M+H), 551.47 (M−H);

1-(6,7-dihydro-5H-benzo[6,7]cyclohepta[1,2-c]pyridazin-3-yl)-$N^3$-((7S)-7-amino-6,7,8,9-tetrahydro-5H-benzo[7]annulen-2-yl)-1H-1,2,4-triazole-3,5-diamine, compound #15, formic acid salt $^1$H NMR (DMSO-$d_6$, 300 MHz) 9.11 (s, 1H, NH), 7.93 (s, 1H), 7.65 (m, 3H), 7.72 (d, 1H), 7.47 (m, 2H), 7.38 (m, 1H), 7.27 (s, 1H), 7.03 (d, 1H), 3.32 (s, 1H), 2.71 (m, 4H), 2.65-2.45 (m, 4H), 2.21 (m, 4H), 1.29 (m, 2H) ppm; MS (ES) 553.65 (M+H), 551.37 (M−H);

free base MS (ES) 453.65 (M+H), 451.39 (M–H); trifluoroacetic acid salt MS (ES) 453.14 (M+H), 451.23 (M–H);

1-(6,7-dihydro-5H-benzo[6,7]cyclohepta[1,2-c]pyridazin-3-yl)-N$^3$-((7s)-7-(di(cyclopropylmethyl)amino)-6,7,8,9-tetrahydro-5H-benzo[7]annulene-2-yl)-1H-1,2,4-triazole-3,5-diamine, compound #16, $^1$H NMR (DMSO-d$_6$, 300 MHz) 9.12 (s, 1H, NH), 7.95 (s, 1H), 7.82 (s, 2H, NH$_2$), 7.71 (m, 1H), 7.45 (m, 3H), 7.31 (m, 2H), 7.05 (d, 2H), 3.75 (t, 1H), 2.96 (m, 4H), 2.73 (m, 4H), 2.65-2.42 (m, 4H), 2.23 (m, 4H), 1.31 (m, 2H), 1.08 (s br, 2H), 0.61 (d, 4H), 0.29 (d, 4H) ppm; MS (ES) 561.30 (M+H), 559.42 (M–H);

1-(6,7-dihydro-5H-benzo[6,7]cyclohepta[1,2-c]pyridazin-3-yl)-N$^3$-((7S)-7-((2-methylpropyl)amino)-6,7,8,9-tetrahydro-5H-benzo[7]annulene-2-yl)-1H-1,2,4-triazole-3,5-diamine, compound #17, $^1$H NMR (DMSO-d$_6$, 300 MHz): 9.13 (s, 1H), 8.25 (s br, 2H), 7.81-8.00 (m, 3H), 7.66-7.76 (m, 1H), 7.41-7.53 (m, 3H), 7.27-7.39 (m, 2H), 6.97-7.11 (m, 1H), 3.19-3.47 (m, 1H), 2.66-2.86 (m, 6H), 2.43-2.65 (m, 7H), 2.14-2.37 (m, 4H), 1.82-1.99 (m, 1H), 1.20-1.47 (m, 2H), 0.93 (d, J=6.6 Hz, 6H) ppm; MS (ES) 509.23 (M+H), 507.36 (M–H);

1-(6,7-dihydro-5H-benzo[6,7]cyclohepta[1,2-c]pyridazin-3-yl)-N$^3$-((7S)-7-((propyl)amino)-6,7,8,9-tetrahydro-5H-benzo[7]annulene-2-yl)-1H-1,2,4-triazole-3,5-diamine, compound #18, $^1$H NMR (DMSO-d$_6$, 300 MHz): 9.06-9.18 (m, 1H), 8.19-8.40 (m, 2H), 7.76-7.99 (m, 3H), 7.23-7.54 (m, 5H), 7.03 (d, 1H), 3.20-3.44 (m, 1H), 2.83-3.00 (m, 2H), 2.66-2.82 (m, 4H), 2.51-2.66 (m, 4H), 2.11-2.34 (m, 4H), 1.46-1.73 (m, 2H), 1.19-1.44 (m, 2H), 0.91 (s, 3H) ppm; MS (ES) 495.24 (M+H), 493.38 (M–H);

1-(6,7-dihydro-5H-benzo[6,7]cyclohepta[1,2-c]pyridazin-3-yl)-N$^3$-((7S)-7-(dipropylamino)-6,7,8,9-tetrahydro-5H-benzo[7]annulene-2-yl)-1H-1,2,4-triazole-3,5-diamine, compound #19, $^1$H NMR (DMSO-d$_6$, 300 MHz): 9.12 (s, 1H), 8.67-8.85 (m, 1H), 7.77-8.02 (m, 3H), 7.65-7.76 (m, 1H), 7.25-7.56 (m, 5H), 7.05 (d, J=8.3 Hz, 1H), 3.47-3.70 (m, 1H), 2.99-3.18 (m, 2H), 2.83-2.98 (m, 2H), 2.66-2.83 (m, 4H), 2.50-2.66 (m, 5H), 2.10-2.34 (m, 4H), 1.34-1.78 (m, 6H), 0.88 (t, J=7.2 Hz, 5H) ppm; MS (ES) 537.30 (M+H), 535.49 (M–H);

1-(6,7-dihydro-5H-benzo[6,7]cyclohepta[1,2-c]pyridazin-3-yl)-N$^3$-((7S)-7-(diethylamino)-6,7,8,9-tetrahydro-5H-benzo[7]annulene-2-yl)-1H-1,2,4-triazole-3,5-diamine, compound #20, $^1$H NMR (DMSO-d$_6$, 300 MHz): 9.10 (s, 1H), 7.94 (s, 1H), 7.83 (s br, 2H), 7.67-7.75 (m, 1H), 7.41-7.53 (m, 3H), 7.29-7.41 (m, 2H), 7.05 (d, 1H), 3.52-3.68 (m, 2H), 2.93-3.27 (m, 4H), 2.66-2.85 (m, 4H), 2.50-2.65 (m, 4H), 2.11-2.31 (m, 5H), 1.33-1.60 (m, 2H), 1.09-1.29 (m, 7H) ppm; MS (ES) 509.23 (M+H), 507.35 (M–H);

1-(6,7-dihydro-5H-benzo[6,7]cyclohepta[1,2-c]pyridazin-3-yl)-N$^3$-((7S)-7-(cyclohexylamino)-6,7,8,9-tetrahydro-5H-benzo[7]annulene-2-yl)-1H-1,2,4-triazole-3,5-diamine, compound #21, MS (ES) 535.30 (M+H), 533.46 (M–H);

1-(6,7-dihydro-5H-benzo[6,7]cyclohepta[1,2-c]pyridazin-3-yl)-N$^3$-((7S)-7-(cyclopentylamino)-6,7,8,9-tetrahydro-5H-benzo[7]annulene-2-yl)-1H-1,2,4-triazole-3,5-diamine, compound #22, MS (ES) 521.28 (M+H), 519.28 (M–H);

1-(6,7-dihydro-5H-benzo[6,7]cyclohepta[1,2-c]pyridazin-3-yl)-N$^3$-((7S)-7-((1-cyclopentylethyl)amino)-6,7,8,9-tetrahydro-5H-benzo[7]annulene-2-yl)-1H-1,2,4-triazole-3,5-diamine, compound #23, MS (ES) 563.30 (M+H);

1-(6,7-dihydro-5H-benzo[6,7]cyclohepta[1,2-c]pyridazin-3-yl)-N$^3$-((7S)-7-(2-propylamino)-6,7,8,9-tetrahydro-5H-benzo[7]annulene-2-yl)-1H-1,2,4-triazole-3,5-diamine, compound #24, $^1$H NMR (DMSO-d$_6$, 300 MHz): 9.09 (s, 1H), 8.32 (s, 1H), 7.94 (s, 1H), 7.84 (s, 2H), 7.63-7.77 (m, 1H), 7.40-7.52 (m, 2H), 7.36 (s br, 1H), 7.28 (s, 1H), 7.01 (d, 1H), 3.16-3.35 (m, 2H), 3.10-3.16 (m, 1H), 2.65-2.80 (m, 4H), 2.56-2.65 (m, 2H), 2.07-2.33 (m, 5H), 1.19-1.40 (m, 2H), 1.16 (d, J=6.3 Hz, 6H) ppm; MS (ES) 495.26 (M+H), 493.37 (M–H);

1-(6,7-dihydro-5H-benzo[6,7]cyclohepta[1,2-c]pyridazin-3-yl)-N$^3$-((7S)-7-((3,3-dimethylbut-2-yl)amino)-6,7,8,9-tetrahydro-5H-benzo[7]annulene-2-yl)-1H-1,2,4-triazole-3,5-diamine, compound #25, MS (ES) 536.18 (M);

1-(6,7-dihydro-5H-benzo[6,7]cyclohepta[1,2-c]pyridazin-3-yl)-N$^3$-((7S)-7-((cyclohexylmethyl)amino)-6,7,8,9-tetrahydro-5H-benzo[7]annulene-2-yl)-1H-1,2,4-triazole-3,5-diamine, compound #26, MS (ES) 549.28 (M+H), 547.29 (M–H);

1-(6,7-dihydro-5H-benzo[6,7]cyclohepta[1,2-c]pyridazin-3-yl)-N$^3$-((7S)-7-(di(cyclohexylmethyl)amino)-6,7,8,9-tetrahydro-5H-benzo[7]annulene-2-yl)-1H-1,2,4-triazole-3,5-diamine, compound #27, MS (ES) 645.43 (M+H), 643.51 (M–H);

1-(6,7-dihydro-5H-benzo[6,7]cyclohepta[1,2-c]pyridazin-3-yl)-N$^3$-((7S)-7-((5-chlorothien-2-yl)methyl)amino-6,7,8,9-tetrahydro-5H-benzo[7]annulene-2-yl)-1H-1,2,4-triazole-3,5-diamine, compound #28, $^1$H NMR (DMSO-d$_6$, 300 MHz): 9.12 (s, 1H), 8.86 (s br, 2H), 7.66-7.99 (m, 3H), 7.26-7.53 (m, 4H), 7.17 (d, 2H), 7.04 (d, 1H), 4.43 (s br, 2H), 3.21-3.36 (m, 2H), 2.65-2.86 (m, 7H), 2.13-2.39 (m, 4H), 1.17-1.50 (m, 2H) ppm; MS (ES) 583.15 (M+H), 581.28 (M–H);

1-(6,7-dihydro-5H-benzo[6,7]cyclohepta[1,2-c]pyridazin-3-yl)-N$^3$-((7S)-7-((2-carboxyphenyl)methyl)amino-6,7,8,9-tetrahydro-5H-benzo[7]annulene-2-yl)-1H-1,2,4-triazole-3,5-diamine, compound #29, MS (ES) 587.26 (M+H);

1-(6,7-dihydro-5H-benzo[6,7]cyclohepta[1,2-c]pyridazin-3-yl)-N$^3$-((7S)-7-((3-bromophenyl)methyl)amino-6,7,8,9-tetrahydro-5H-benzo[7]annulene-2-yl)-1H-1,2,4-triazole-3,5-diamine, compound #30, $^1$H NMR (DMSO-d$_6$, 300 MHz): 9.09 (s, 1H), 8.01 (s, 1H), 7.67-7.96 (m, 6H), 7.27-7.50 (m, 5H), 7.03 (d, 1H), 6.50 (s, 1H), 4.12 (s br, 1H), 3.05-3.20 (m, 3H), 2.65-2.79 (m, 4H), 2.55-2.64 (m, 2H), 2.15-2.37 (m, 4H), 1.17-1.46 (m, 3H) ppm; MS (ES) 623.00 (M+H), 619.06 (M–H);

1-(6,7-dihydro-5H-benzo[6,7]cyclohepta[1,2-c]pyridazin-3-yl)-N$^3$-((7S)-7-(dimethylamino)-6,7,8,9-tetrahydro-5H-benzo[7]annulene-2-yl)-1H-1,2,4-triazole-3,5-diamine, compound #31, $^1$H NMR (DMSO-d$_6$, 300 MHz): 9.06 (s, 1H), 8.25 (s br, 2H), 7.81-8.01 (m, 3H), 7.65-7.78 (m, 2H), 7.25-7.51 (m, 2H), 6.97-7.08 (m, 1H), 4.86-5.00 (m, 1H), 3.99-4.08 (m, 1H), 2.66-2.85 (m, 2H), 2.52-2.65 (m, 4H), 2.15-2.36 (m, 5H), 1.87-2.12 (m, 5H), 1.12-1.48 (m, 3H) ppm; MS (ES) 481.10 (M+H), 479.13 (M–H);

1-(6,7-dihydro-5H-benzo[6,7]cyclohepta[1,2-c]pyridazin-3-yl)-N$^3$-((7S)-7-(cyclobutylamino)-6,7,8,9-tetrahydro-5H-benzo[7]annulene-2-yl)-1H-1,2,4-triazole-3,5-diamine, compound #32, MS (ES) 507.15 (M+H), 505.24 (M–H);

1-(6,7-dihydro-5H-benzo[6,7]cyclohepta[1,2-c]pyridazin-3-yl)-N$^3$-((7S)-7-(3-pentylamino)-6,7,8,9-tetrahydro-5H-benzo[7]annulene-2-yl)-1H-1,2,4-triazole-3,5-diamine, compound #33, MS (ES) 523.16 (M+H), 521.27 (M–H);

1-(6,7-dihydro-5H-benzo[6,7]cyclohepta[1,2-c]pyridazin-3-yl)-N$^3$-((7S)-7-((2,2-dimethylpropyl)amino)-6,7,8,9-tetrahydro-5H-benzo[7]annulene-2-yl)-1H-1,2,4-triazole-3,5-diamine, compound #34, $^1$H NMR (DMSO-d$_6$, 300 MHz): 9.05 (s, 1H), 8.29 (s, 1H), 7.93 (s, 1H), 7.85 (s br, 2H), 7.61-7.75 (m, 1H), 7.32-7.49 (m, 3H), 7.28 (s, 1H), 6.99 (d, 1H), 2.82-2.96 (m, 1H), 2.65-2.78 (m, 3H), 2.56-2.65 (m, 2H), 2.36-2.54 (m, 5H), 2.17-2.33 (m, 2H), 1.99-2.16 (m, 2H), 1.15-1.42 (m, 2H), 0.88 (s, 9H) ppm; MS (ES) 523.16 (M+H), 521.26 (M−H);

1-(6,7-dihydro-5H-benzo[6,7]cyclohepta[1,2-c]pyridazin-3-yl)-N$^3$-((7S)-7-(di(cyclopentylmethyl)amino)-6,7,8,9-tetrahydro-5H-benzo[7]annulene-2-yl)-1H-1,2,4-triazole-3,5-diamine, compound #35, MS (ES) 617.28 (M+H), 615.31 (M−H);

1-(6,7-dihydro-5H-benzo[6,7]cyclohepta[1,2-c]pyridazin-3-yl)-N$^3$-((7S)-7-((cyclopentylmethyl)amino)-6,7,8,9-tetrahydro-5H-benzo[7]annulene-2-yl)-1H-1,2,4-triazole-3,5-diamine, compound #36, $^1$H NMR (DMSO-d$_6$, 300 MHz): 9.07 (s, 1H), 8.34 (s, 1H), 7.94 (s, 1H), 7.84 (s br, 2H), 7.66-7.75 (m, 1H), 7.33-7.53 (m, 3H), 7.28 (s, 1H), 7.00 (d, 1H), 2.87-3.13 (m, 1H), 2.40-2.84 (m, 10H), 1.92-2.33 (m, 5H), 1.63-1.80 (m, 2H), 1.39-1.63 (m, 4H), 1.05-1.38 (m, 4H) ppm; MS (ES) 535.18 (M+H), 533.16 (M−H);

1-(6,7-dihydro-5H-benzo[6,7]cyclohepta[1,2-c]pyridazin-3-yl)-N$^3$-((7S)-7-(di(bicyclo[2.2.1]hept-2-en-5-ylmethyl)amino)-6,7,8,9-tetrahydro-5H-benzo[7]annulene-2-yl)-1H-1,2,4-triazole-3,5-diamine, compound #37, MS (ES) 665.26 (M+H), 663.40 (M−H);

1-(6,7-dihydro-5H-benzo[6,7]cyclohepta[1,2-c]pyridazin-3-yl)-N$^3$-((7S)-7-((bicyclo[2.2.1]hept-2-en-5-ylmethyl)amino)-6,7,8,9-tetrahydro-5H-benzo[7]annulene-2-yl)-1H-1,2,4-triazole-3,5-diamine, compound #38, $^1$H NMR (DMSO-d$_6$, 300 MHz): 9.03 (s, 1H), 8.32 (s, 1H), 7.92 (s, 1H), 7.83 (s br, 2H), 7.63-7.75 (m, 1H), 7.32-7.55 (m, 3H), 7.27 (s, 1H), 6.99 (d, 1H), 6.08-6.21 (m, 1H), 5.89-6.01 (m, 1H), 2.83-3.03 (m, 2H), 2.65-2.82 (m, 4H), 2.54-2.65 (m, 4H), 2.29-2.44 (m, 4H), 1.93-2.33 (m, 6H), 1.81 (t, 1H), 1.14-1.37 (m, 4H), 0.39-0.60 (m, 1H) ppm; MS (ES) 559.17 (M+H), 557.39 (M−H);

1-(6,7-dihydro-5H-benzo[6,7]cyclohepta[1,2-c]pyridazin-3-yl)-N$^3$-((7S)-7-(3-methylbutylamino)-6,7,8,9-tetrahydro-5H-benzo[7]annulene-2-yl)-1H-1,2,4-triazole-3,5-diamine, compound #39, $^1$H NMR (DMSO-d$_6$, 300 MHz): 9.08 (s, 1H), 8.34 (s, 1H), 7.93 (s, 1H), 7.86 (s br, 2H), 7.67-7.74 (m, 1H), 7.40-7.51 (m, 3H), 7.33-7.39 (m, 1H), 7.29 (s br, 1H), 7.01 (d, J=8.3 Hz, 1H), 3.08 (s br, 1H), 2.52-2.87 (m, 10H), 2.07-2.33 (m, 4H), 1.52-1.68 (m, 1H), 1.35-1.48 (m, 2H), 1.17-1.34 (m, 2H), 0.87 (d, J=6.3 Hz, 6H) ppm; MS (ES) 523.20 (M+H), 521.27 (M−H);

1-(6,7-dihydro-5H-benzo[6,7]cyclohepta[1,2-c]pyridazin-3-yl)-N$^3$-((7S)-7-(di(3-methylbutyl)amino)-6,7,8,9-tetrahydro-5H-benzo[7]annulene-2-yl)-1H-1,2,4-triazole-3,5-diamine, compound #40, $^1$H NMR (DMSO-d$_6$, 300 MHz): 9.01 (s, 1H), 7.91 (s, 1H), 7.83 (s br, 2H), 7.67-7.74 (m, 1H), 7.39-7.49 (m, 3H), 7.33-7.39 (m, 1H), 7.25-7.31 (m, 1H), 6.99 (d, J=8.3 Hz, 1H), 2.52-2.75 (m, 9H), 2.16-2.38 (m, 7H), 1.86-2.04 (m, 2H), 1.49-1.62 (m, 2H), 1.11-1.28 (m, 5H), 0.83 (d, J=6.6 Hz, 12H) ppm; MS (ES) 593.28 (M+H), 591.33 (M−H);

1-(6,7-dihydro-5H-benzo[6,7]cyclohepta[1,2-c]pyridazin-3-yl)-N$^3$-((7S)-7-(2-ethylbutylamino)-6,7,8,9-tetrahydro-5H-benzo[7]annulene-2-yl)-1H-1,2,4-triazole-3,5-diamine, compound #41, $^1$H NMR (DMSO-d$_6$, 300 MHz): $^1$H NMR (DMSO-d$_6$) d: 9.04 (s, 1H), 8.28 (s, 1H), 7.93 (s, 1H), 7.84 (s br, 2H), 7.66-7.75 (m, 1H), 7.40-7.50 (m, 3H), 7.32-7.40 (m, 1H), 7.29 (s, 1H), 7.01 (d, J=8.3 Hz, 1H), 2.96-3.11 (m, 1H), 2.44-2.82 (m, 13H), 2.06-2.30 (m, 4H), 1.17-1.51 (m, 6H), 0.82 (t, J=7.3 Hz, 6H) ppm; MS (ES) 537.20 (M+H), 535.27 (M−H);

1-(6,7-dihydro-5H-benzo[6,7]cyclohepta[1,2-c]pyridazin-3-yl)-N$^3$-((7S)-7-(but-2-enylamino)-6,7,8,9-tetrahydro-5H-benzo[7]annulene-2-yl)-1H-1,2,4-triazole-3,5-diamine, compound #42, MS (ES) 507.16 (M+H), 505.11 (M−H);

1-(6,7-dihydro-5H-benzo[6,7]cyclohepta[1,2-c]pyridazin-3-yl)-N$^3$-((7S)-7-(butyl(but-2-enyl)amino)-6,7,8,9-tetrahydro-5H-benzo[7]annulene-2-yl)-1H-1,2,4-triazole-3,5-diamine, compound #43, MS (ES) 562.16 (M);

1-(6,7-dihydro-5H-pyrido[2',3':6,7]cyclohepta[1,2-c]pyridazin-3-yl)-N$^5$-((7S)-7-(t-butoxycarbonylamino)-6,7,8,9-tetrahydro-5H-benzo[7]annulene-2-yl)-1H-1,2,4-triazole-3,5-diamine, compound #44, MS (ES) 554.10 (M+H), 552.22 (M−H);

1-(6,7-dihydro-5H-pyrido[2',3':6,7]cyclohepta[1,2-c]pyridazin-3-yl)-N$^3$-(3-fluoro-4-(4-(pyrrolidin-1-yl)piperidin-1-yl)phenyl)-1H-1,2,4-triazole-3,5-diamine, compound #45, $^1$H NMR (DMSO-d$_6$, 300 MHz): 9.23 (s, 1H), 8.54-8.69 (m, 1H), 8.10 (d, 1H), 7.98 (s, 1H), 7.87 (s br, 2H), 7.31-7.56 (m, 3H), 6.97 (t, 1H), 3.38-3.43 (m, 3H), 2.53-2.80 (m, 6H), 2.18-2.41 (m, 5H), 1.97-2.15 (m, 2H), 1.84-1.97 (m, 3H), 1.42-1.76 (m, 4H) ppm; MS (ES) 541.63 (M+H), 539.45 (M−H);

1-(6,7-dihydro-5H-pyrido[2',3':6,7]cyclohepta[1,2-c]pyridazin-3-yl)-N$^3$-((7S)-7-amino-6,7,8,9-tetrahydro-5H-benzo[7]annulene-2-yl)-1H-1,2,4-triazole-3,5-diamine, compound #46, $^1$H NMR (DMSO-d$_6$, 300 MHz) 9.04 (s, 1H), 8.59 (d, 1H), 8.21 (s, 1H), 8.06 (d, 1H), 7.99 (s, 1H), 7.84 (s, 1H), 7.62-7.43 (m, 2H), 7.26 (s, 1H), 6.95 (d, 1H) 2.92 (m, 1H), 2.68-2.42 (m, 4H), 2.44 (s, 2H), 2.29 (m, 2H), 2.05 (m, 2H), 1.29 (m, 2H), 1.01 (m, 4H) ppm; MS (ES) 454.37 (M+H);

1-(6,7-dihydro-5H-pyrido[2',3':6,7]cyclohepta[1,2-c]pyridazin-3-yl)-N$^3$-((7S)-7-(dimethylamino)-6,7,8,9-tetrahydro-5H-benzo[7]annulene-2-yl)-1H-1,2,4-triazole-3,5-diamine, compound #47, $^1$H NMR (DMSO-d$_6$, 300 MHz) 9.03 (s, 1H), 8.53 (d, 1H), 8.25 (s, 1H), 8.11 (d, 1H), 7.95 (s, 1H), 7.88 (s, 1H), 7.51-7.39 (m, 2H), 7.26 (s, 1H), 7.08 (d, 1H), 2.92 (m, 1H), 2.72-2.48 (m, 8H), 2.40 (s, 2H), 2.31 (m, 2H), 2.02 (m, 2H), 1.25 (m, 2H), 1.06 (m, 4H) ppm; MS (ES) 482.08 (M+H), 480.23 (M−H);

1-(6,7-dihydro-5H-pyrido[2',3':6,7]cyclohepta[1,2-c]pyridazin-3-yl)-N$^3$-((7S)-7-(diethylamino)-6,7,8,9-tetrahydro-5H-benzo[7]annulene-2-yl)-1H-1,2,4-triazole-3,5-diamine, compound #48, $^1$H NMR (DMSO-d$_6$, 300 MHz) 9.05 (s, 1H), 8.58 (d, 1H), 8.22 (s, 1H), 8.09 (d, 1H), 7.96 (s, 1H), 7.85 (s, 1H), 7.56-7.38 (m, 2H), 7.28 (s, 1H), 7.03 (d, 1H), 2.98 (m, 1H), 2.79-2.52 (m, 12H), 2.49 (s, 2H), 2.33 (m, 2H), 2.04 (m, 2H), 1.27 (m, 2H), 1.03 (m, 4H) ppm; MS (ES) 510.57 (M+H);

1-(6,7-dihydro-5H-pyrido[2',3':6,7]cyclohepta[1,2-c]pyridazin-3-yl)-N$^3$-((7S)-7-(dipropylamino)-6,7,8,9-tetrahydro-5H-benzo[7]annulene-2-yl)-1H-1,2,4-triazole-3,5-diamine, compound #49, $^1$H NMR (DMSO-d$_6$, 300 MHz) 9.04 (s, 1H), 8.58 (d, 1H), 8.18 (s, 1H), 8.08 (d, 1H), 7.96 (s, 1H), 7.85 (s, 1H), 7.60-7.40 (m, 2H), 7.28 (s, 1H), 6.99 (d, 1H), 2.86-2.56 (m, 10H), 2.41-2.24 (m, 6H), 1.99 (m, 2H), 1.50-1.09 (m, 5H), 0.82 (t, 6H) ppm; MS (ES) 538.15 (M+H), 536.25 (M−H);

1-(6,7-dihydro-5H-pyrido[2',3':6,7]cyclohepta[1,2-c]pyridazin-3-yl)-N$^3$-((7S)-7-(di(cyclopropylmethyl)amino)-6,7,8,9-tetrahydro-5H-benzo[7]annulene-2-yl)-1H-1,2,4-triazole-3,5-diamine, compound #50, $^1$H NMR (DMSO-d$_6$, 300 MHz) 9.05 (s, 1H), 8.60 (d, 1H), 8.21 (s, 1H), 8.09 (d, 1H), 7.96 (s, 1H), 7.85 (s, 1H), 7.55-7.39 (m, 2H), 7.26 (s, 1H), 7.00 (d, 1H), 3.10 (t, 2H), 2.77-2.54 (m, 8H), 2.45-2.22 (m, 6H), 2.01 (m, 4H), 1.30-1.09 (m, 2H), 0.84 (m, 2H), 0.43 (d, 3H), 0.10 (d, 2H) ppm; MS (ES) 562.16 (M+H), 560.39 (M−H);

1-(6,7-dihydro-5H-pyrido[2',3':6,7]cyclohepta[1,2-c]py-ridazin-3-yl)-N$^3$-((7S)-7-(di(3-methylbutyl)amino)-6,7,8,9-tetrahydro-5H-benzo[7]annulene-2-yl)-1H-1,2,4-triazole-3,5-diamine, compound #51, $^1$H NMR (DMSO-d$_6$, 300 MHz) 9.04 (s, 1H), 8.59 (d, 1H), 8.21 (s, 1H), 8.06 (d, 1H), 7.99 (s, 1H), 7.84 (s, 1H), 7.62-7.43 (m, 2H), 7.26 (s, 1H), 6.95 (d, 1H), 2.83-2.59 (m, 6H), 2.51-2.31 (m, 6H), 2.01 (m, 2H), 1.66-1.38 (m, 5H), 1.24 (m, 6H), 0.88 (d, 6H), 0.83 (d, 6H) ppm; MS (ES) 594.21 (M+H); 592.25 (M−H);

1-(6,7-dihydro-5H-pyrido[2',3':6,7]cyclohepta[1,2-c]py-ridazin-3-yl)-N$^3$-((7S)-7-(cyclobutylamino)-6,7,8,9-tetrahydro-5H-benzo[7]annulene-2-yl)-1H-1,2,4-triazole-3,5-diamine, compound #52, $^1$H NMR (DMSO-d$_6$, 300 MHz) 9.04 (s, 1H), 8.59 (d, 1H), 8.29 (s, 1H), 8.10 (d, 1H), 7.96 (s, 1H), 7.85 (s, 1H), 7.55-7.39 (m, 2H), 7.24 (s, 1H), 6.99 (d, 1H), 2.93-2.53 (m, 8H), 2.31 (m, 4H), 2.11 (m, 2H), 1.96 (m, 2H), 1.80 (m, 2H), 1.62 (m, 2H), 1.32-1.10 (m, 2H) ppm; MS (ES) 508.05 (M+H), 506.13 (M−H);

1-(6,7-dihydro-5H-pyrido[2',3':6,7]cyclohepta[1,2-c]py-ridazin-3-yl)-N$^3$-((7S)-7-(cyclohexylamino)-6,7,8,9-tetrahydro-5H-benzo[7]annulene-2-yl)-1H-1,2,4-triazole-3,5-diamine, compound #53, $^1$H NMR (DMSO-d$_6$, 300 MHz) 9.06 (s, 1H), 8.60 (d, 1H), 8.31 (s, 1H), 8.10 (d, 1H), 7.95 (s, 1H), 7.85 (s, 1H), 7.54-7.39 (m, 2H), 7.27 (s, 1H), 6.97 (d, 1H), 2.89-2.58 (m, 8H), 2.52 (m, 2H), 2.36 (m, 2H), 2.09 (m, 2H), 1.87 (m, 2H), 1.70 (m, 2H), 1.56 (m, 2H), 1.36-1.01 (m, 6H) ppm; MS (ES) 536.12 (M+H);

1-(6,7-dihydro-5H-pyrido[2',3':6,7]cyclohepta[1,2-c]py-ridazin-3-yl)-N$^3$-((7S)-7-((methylethyl)amino)-6,7,8,9-tetrahydro-5H-benzo[7]annulene-2-yl)-1H-1,2,4-triazole-3,5-diamine, compound #54 $^1$H NMR (DMSO-d$_6$, 300 MHz) 9.04 (s, 1H), 8.57 (d, 1H), 8.32 (s, 1H), 8.09 (d, 1H), 7.94 (s, 1H), 7.84 (s, 1H), 7.57-7.38 (m, 2H), 7.22 (s, 1H), 6.96 (d, 1H), 3.18-3.32 (m, 2H), 3.16-3.12 (m, 1H), 2.80-2.64 (m, 4H), 2.66-2.56 (m, 2H), 2.35-2.07 (m, 5H), 1.41-1.08 (m, 2H), 1.15 (d, J=6.3 Hz, 6H) ppm; MS (ES) 496.09 (M+H), 494.12 (M−H);

1-(6,7-dihydro-5H-pyrido[2',3':6,7]cyclohepta[1,2-c]py-ridazin-3-yl)-N$^3$-((7S)-7-(cyclopentylamino)-6,7,8,9-tetrahydro-5H-benzo[7]annulene-2-yl)-1H-1,2,4-triazole-3,5-diamine, compound #55, $^1$H NMR (DMSO-d$_6$, 300 MHz) 9.05 (s, 1H), 8.61 (d, 1H), 8.21 (s, 1H), 8.11 (d, 1H), 7.96 (s, 1H), 7.84 (s, 1H), 7.57-7.39 (m, 2H), 7.29 (s, 1H), 6.96 (d, 1H), 3.36 (m, 2H) 2.81-2.52 (m, 8H), 2.45-2.21 (m, 6H), 2.01 (m, 2H), 1.87-1.44 (m, 4H), 1.29 (m, 2H) ppm; MS (ES) 522.12 (M+H), 520.31 (M−H); and 1-(6,7-dihydro-5H-pyrido[2',3':6,7]cyclohepta[1,2-c]py-ridazin-3-yl)-N$^3$-((7S)-7-(2-butylamino)-6,7,8,9-tetrahydro-5H-benzo[7]annulene-2-yl)-1H-1,2,4-triazole-3,5-diamine, compound #56, $^1$H NMR (DMSO-d$_6$, 300 MHz) 9.06 (s, 1H), 8.60 (d, 1H), 8.27 (s, 1H), 8.07 (d, 1H), 7.98 (s, 1H), 7.87 (s, 1H), 7.59-7.43 (m, 2H), 7.20 (s, 1H), 7.01 (d, 1H), 3.28 (m, 2H), 2.95-2.63 (m, 8H), 2.19 (m, 5H), 1.75 (m, 2H), 1.41-1.11 (m, 2H), 0.95 (t, 3H) ppm; MS (ES) 510.09 (M+H), 508.38 (M−H).

Biological Example 1

Phospho-Akt in-Cell Western Assay

The compounds of the invention were tested in the following assay for their ability to inhibit Axl activity.
Reagents and Buffers:
Cell culture plate: 96 well assay plate (Corning 3610), white, clear bottom, tissue-culture treated.
Cells: Hela cells.
Starvation medium: For Axl stimulation: 0.5% FCS (fetal calf serum) in DMEM, plus Axl/Fc (extracellular domain of AXL fused to imunoglobulin Fc region) (R&D, 154-AL) 500 ng/mL.
For EGF (epidermal growth factor) stimulation: 0.5% FCS in DMEM (Dulbecco's modified Eagles medium).
Poly-L-Lysine 0.01% solution (the working solution): 10 µg/ml, dilute In PBS (phosphate buffered saline).
Axl antibody cross-linking:
  1$^{st}$: Mouse anti-Axl (R&D, MAB154).
  2$^{nd}$: Biotin-SP-conjugated AffiniPure goat anti-mouse IgG (H+L) (Jackson ImmunoResearch #115-065-003).
Fixing buffer: 4% formaldehyde in PBS.
Wash buffer: 0.1% TritonX-100 in PBS.
Quenching buffer: 3% H$_2$O$_2$, 0.1% Azide in wash buffer, Azide and hydrogen peroxide (H$_2$O$_2$) are added fresh.
Blocking buffer: 5% BSA in TBST (tris buffered saline plus 0.1% Tween 20).
Primary antibody: Rabbit anti-human Phospho-Akt antibody (Cell Signaling 9271): 1×250 diluted in blocking buffer.
Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.
Chemiluminescent working solution (Pierce, 37030): SuperSignal ELISA (enzyme linked immunosorbant assay) Pico Chemiluminescent substrate.
Crystal Violet solution: Stock: 2.5% Crystal violet in methanol, filtered and kept at ambient temperature. The working solution: dilute the stock 1:20 with PBS immediately before use.
10% SDS: working solution: 5% SDS (sodium dodecylsulfate), diluted in PBS
Methods:
Day 1:
A 96 well TC (tissue culture treated) plate was coated with 10 µg/mL poly-L-Lysine at 37° C. for 30 min, washed twice with PBS, and air-dried for 5 minutes before cells were added. Hela cells were seeded at 10,000 cells/well and the cells were starved in 100 µL starvation medium containing Axl/Fc for 24 hrs.
Day 2:
The cells were pre-treated with test compounds by adding 100 µL of 2× test compound to the starvation medium on the cells. The cells were incubated at 37° C. for 1 hr before stimulation.
The cells were stimulated by Axl-antibody cross-linking as follows: A 5× 1$^{st}$/2$^{nd}$ Axl antibody mixture was made (37.5 µg/mL 1$^{st}$/100 µg/mL 2$^{nd}$) in starvation medium and nutated at 4° C. with thorough mixing for 1-2 hours for clustering. The resulting mix was warmed to 37° C. 50 µL of 5× Axl 1$^{st}$/2$^{nd}$ of antibody cluster was added to the cells and the cells were incubated at 37° C. for 5 min.
After 5 minutes stimulation, the plate was flicked to remove medium and the plate was tapped onto paper towels. Formaldehyde (4.0% in PBS, 100 µL) was added to fix the cells and the cells were incubated at ambient temperature for 20 min without shaking.
The cells were washed with a plate washer buffer to remove the formaldehyde solution. The plate was flicked to removed excess wash buffer and tapped onto paper towels. Quenching buffer (100 µL) was added to each well and the cells were incubated at ambient temperature for 20 minutes without shaking.

The cells were washed with a plate washer buffer to remove the quenching buffer. Blocking buffer (100 μL) was added and the cells were incubated at ambient temperature for at least an hour with gentle shaking.

The cells were washed with a plate washer buffer and diluted primary antibody (50 μL) was added to each well (blocking buffer was added to the negative control wells instead). The plates were incubated overnight at 4° C. with gentle shaking.

Day 3:

The wash buffer was removed, diluted secondary antibody (100 μL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 μL: 40 μL A and 40 μL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 μL) was added to each well and the cells were incubated at ambient temperature for 30 min. The crystal violet solution was removed, and the wells were rinsed with PBS, then washed 3× with PBS (200 μL) for 5 minutes each.

5% SDS solution (70 μL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

The results of the ability of the compounds of the invention to inhibit Axl activity, when tested in the above assay, are shown in the following Tables wherein the level of activity (i.e., the $IC_{50}$) for each compound is indicated in each Table. The compound numbers in the Tables referred to the compounds disclosed herein as being prepared by the methods disclosed herein:

TABLE 1

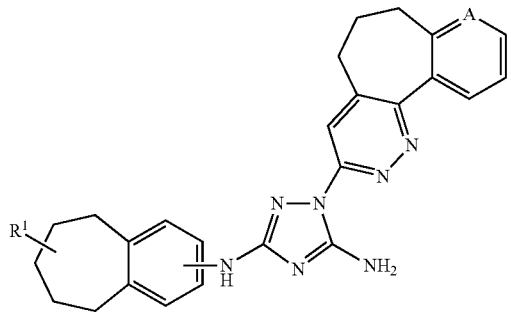

(Ia)

| Cpd # | Compound Name | A | R$^1$ | IC$_{50}$ |
|---|---|---|---|---|
| 1 | 1-(6,7-dihydro-5H-benzo[6,7]cyclohepta[1,2-c]pyridazin-3-yl)-N$^3$-(7-(acetamido)-6,7,8,9-tetrahydro-5H-benzo[7]annulene-2-yl)-1H-1,2,4-triazole-3,5-diamine | =C(H)— | (HN-C(=O)-CH$_3$) | A |
| 2 | 1-(6,7-dihydro-5H-benzo[6,7]cyclohepta[1,2-c]pyridazin-3-yl)-N$^3$-(7-((2R)-2-(methoxycarbonyl)pyrrolidin-1-yl)-6,7,8,9-tetrahydro-5H-benzo[7]annulene-2-yl)-1H-1,2,4-triazole-3,5-diamine | =C(H)— | (pyrrolidine-2-carboxylic acid methyl ester) | A |
| 3 | 1-(6,7-dihydro-5H-benzo[6,7]cyclohepta[1,2-c]pyridazin-3-yl)-N$^3$-(7-(4,4-difluoropiperidin-1-yl)-6,7,8,9-tetrahydro-5H-benzo[7]annulene-2-yl)-1H-1,2,4-triazole-3,5-diamine | =C(H)— | (4,4-difluoropiperidinyl) | B |
| 4 | 1-(6,7-dihydro-5H-benzo[6,7]cyclohepta[1,2-c]pyridazin-3-yl)-N$^3$-(7-((methoxycarbonylmethyl)(methyl)amino)-6,7,8,9-tetrahydro-5H-benzo[7]annulene-2-yl)-1H-1,2,4-triazole-3,5-diamine | =C(H)— | (N-methyl-N-(methoxycarbonylmethyl)amino) | A |

TABLE 1-continued (Ia)

| Cpd # | Compound Name | A | R¹ | IC$_{50}$ |
|---|---|---|---|---|
| 5 | 1-(6,7-dihydro-5H-benzo[6,7]cyclohepta[1,2-c]pyridazin-3-yl)-N³-(7-((2R)-2-(carboxy)pyrrolidin-1-yl)-6,7,8,9-tetrahydro-5H-benzo[7]annulene-2-yl)-1H-1,2,4-triazole-3,5-diamine | =C(H)— | (2R)-2-carboxypyrrolidin-1-yl | A |
| 6 | 1-(6,7-dihydro-5H-benzo[6,7]cyclohepta[1,2-c]pyridazin-3-yl)-N³-(7-(4-(ethoxycarbonyl)piperidin-1-yl)-6,7,8,9-tetrahydro-5H-benzo[7]annulene-2-yl)-1H-1,2,4-triazole-3,5-diamine | =C(H)— | 4-(ethoxycarbonyl)piperidin-1-yl | A |
| 7 | 1-(6,7-dihydro-5H-benzo[6,7]cyclohepta[1,2-c]pyridazin-3-yl)-N³-(7-(4-(carboxy)piperidin-1-yl)-6,7,8,9-tetrahydro-5H-benzo[7]annulene-2-yl)-1H-1,2,4-triazole-3,5-diamine | =C(H)— | 4-(carboxy)piperidin-1-yl | A |
| 8 | 1-(6,7-dihydro-5H-benzo[6,7]cyclohepta[1,2-c]pyridazin-3-yl)-N³-(7-((carboxymethyl)(methyl)amino)-6,7,8,9-tetrahydro-5H-benzo[7]annulene-2-yl)-1H-1,2,4-triazole-3,5-diamine | =C(H)— | (carboxymethyl)(methyl)amino | B |
| 9 | 1-(6,7-dihydro-5H-benzo[6,7]cyclohepta[1,2-c]pyridazin-3-yl)-N³-(7-(4-(ethoxycarbonylmethyl)piperazin-1-yl)-6,7,8,9-tetrahydro-5H-benzo[7]annulene-2-yl)-1H-1,2,4-triazole-3,5-diamine | =C(H)— | 4-(ethoxycarbonylmethyl)piperazin-1-yl | A |
| 10 | 1-(6,7-dihydro-5H-benzo[6,7]cyclohepta[1,2-c]pyridazin-3-yl)-N³-(7-(4-(carboxymethyl)piperazin-1-yl)-6,7,8,9-tetrahydro-5H-benzo[7]annulene-2-yl)-1H-1,2,4-triazole-3,5-diamine | =C(H)— | 4-(carboxymethyl)piperazin-1-yl | B |
| 11 | 1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulene-1-yl)-1H-1,2,4-triazole-3,5-diamine | =C(H)— | pyrrolidin-1-yl | D |
| 13 | 1-(6,7-dihydro-5H-benzo[6,7]cyclohepta[1,2-c]pyridazin-3-yl)-N³-((7S)-7-(t-butoxycarbonylamino)-6,7,8,9-tetrahydro-5H-benzo[7]annulene-2-yl)-1H-1,2,4-triazole-3,5-diamine | =C(H)— | (7S)-t-butoxycarbonylamino | D |

TABLE 1-continued

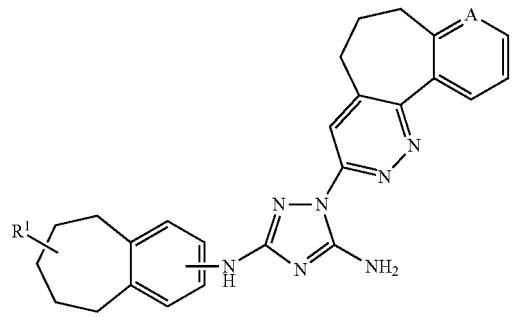
(Ia)

| Cpd # | Compound Name | A | R¹ | IC$_{50}$ |
|---|---|---|---|---|
| 15 | 1-(6,7-dihydro-5H-benzo[6,7]cyclohepta[1,2-c]pyridazin-3-yl)-N³-((7S)-7-amino-6,7,8,9-tetrahydro-5H-benzo[7]annulene-2-yl)-1H-1,2,4-triazole-3,5-diamine | =C(H)— | H$_2$N—* | B |
| 16 | 1-(6,7-dihydro-5H-benzo[6,7]cyclohepta[1,2-c]pyridazin-3-yl)-N³-((7s)-7-(di(cyclopropylmethyl)amino)-6,7,8,9-tetrahydro-5H-benzo[7]annulene-2-yl)-1H-1,2,4-triazole-3,5-diamine | =C(H)— | (di(cyclopropylmethyl)amino) | A |
| 17 | 1-(6,7-dihydro-5H-benzo[6,7]cyclohepta[1,2-c]pyridazin-3-yl)-N³-((7S)-7-((2-methylpropyl)amino)-6,7,8,9-tetrahydro-5H-benzo[7]annulene-2-yl)-1H-1,2,4-triazole-3,5-diamine | =C(H)— | (2-methylpropyl)amino | A |
| 18 | 1-(6,7-dihydro-5H-benzo[6,7]cyclohepta[1,2-c]pyridazin-3-yl)-N³-((7S)-7-((propyl)amino)-6,7,8,9-tetrahydro-5H-benzo[7]annulene-2-yl)-1H-1,2,4-triazole-3,5-diamine | =C(H)— | propylamino | A |
| 19 | 1-(6,7-dihydro-5H-benzo[6,7]cyclohepta[1,2-c]pyridazin-3-yl)-N³-((7S)-7-(dipropylamino)-6,7,8,9-tetrahydro-5H-benzo[7]annulene-2-yl)-1H-1,2,4-triazole-3,5-diamine | =C(H)— | dipropylamino | A |
| 20 | 1-(6,7-dihydro-5H-benzo[6,7]cyclohepta[1,2-c]pyridazin-3-yl)-N³-((7S)-7-(diethylamino)-6,7,8,9-tetrahydro-5H-benzo[7]annulene-2-yl)-1H-1,2,4-triazole-3,5-diamine | =C(H)— | diethylamino | A |
| 21 | 1-(6,7-dihydro-5H-benzo[6,7]cyclohepta[1,2-c]pyridazin-3-yl)-N³-((7S)-7-(cyclohexylamino)-6,7,8,9-tetrahydro-5H-benzo[7]annulene-2-yl)-1H-1,2,4-triazole-3,5-diamine | =C(H)— | cyclohexylamino | A |
| 22 | 1-(6,7-dihydro-5H-benzo[6,7]cyclohepta[1,2-c]pyridazin-3-yl)-N³-((7S)-7-(cyclopentylamino)-6,7,8,9-tetrahydro-5H-benzo[7]annulene-2-yl)-1H-1,2,4-triazole-3,5-diamine | =C(H)— | cyclopentylamino | A |

TABLE 1-continued

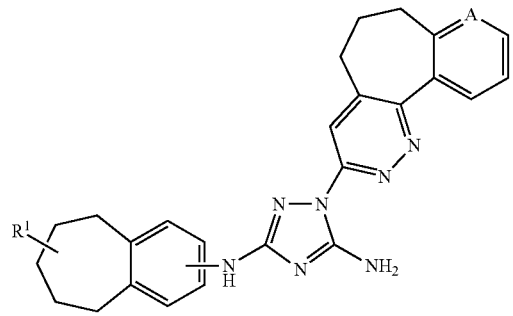

(Ia)

| Cpd # | Compound Name | A | R¹ | IC$_{50}$ |
|---|---|---|---|---|
| 23 | 1-(6,7-dihydro-5H-benzo[6,7]cyclohepta[1,2-c]pyridazin-3-yl)-N³-((7S)-7-((1-cyclopentylethyl)amino)-6,7,8,9-tetrahydro-5H-benzo[7]annulen-2-yl)-1H-1,2,4-triazole-3,5-diamine | =C(H)— | cyclohexyl-CH(CH₃)-NH- | B |
| 24 | 1-(6,7-dihydro-5H-benzo[6,7]cyclohepta[1,2-c]pyridazin-3-yl)-N³-((7S)-7-((methylethyl)amino)-6,7,8,9-tetrahydro-5H-benzo[7]annulen-2-yl)-1H-1,2,4-triazole-3,5-diamine | =C(H)— | (H₃C)₂CH-NH- | A |
| 25 | 1-(6,7-dihydro-5H-benzo[6,7]cyclohepta[1,2-c]pyridazin-3-yl)-N³-((7S)-7-((3,3-dimethylbut-2-yl)amino)-6,7,8,9-tetrahydro-5H-benzo[7]annulen-2-yl)-1H-1,2,4-triazole-3,5-diamine | =C(H)— | (H₃C)₃C-CH(CH₃)-NH- | B |
| 26 | 1-(6,7-dihydro-5H-benzo[6,7]cyclohepta[1,2-c]pyridazin-3-yl)-N³-((7S)-7-((cyclohexylmethyl)amino)-6,7,8,9-tetrahydro-5H-benzo[7]annulen-2-yl)-1H-1,2,4-triazole-3,5-diamine | =C(H)— | cyclohexyl-CH₂-NH- | A |
| 27 | 1-(6,7-dihydro-5H-benzo[6,7]cyclohepta[1,2-c]pyridazin-3-yl)-N³-((7S)-7-(di(cyclohexylmethyl)amino)-6,7,8,9-tetrahydro-5H-benzo[7]annulen-2-yl)-1H-1,2,4-triazole-3,5-diamine | =C(H)— | (cyclohexyl-CH₂)₂N- | C |
| 28 | 1-(6,7-dihydro-5H-benzo[6,7]cyclohepta[1,2-c]pyridazin-3-yl)-N³-((7S)-7-((5-chlorothien-2-yl)methyl)amino-6,7,8,9-tetrahydro-5H-benzo[7]annulen-2-yl)-1H-1,2,4-triazole-3,5-diamine | =C(H)— | (5-Cl-thien-2-yl)-CH₂-NH- | B |
| 29 | 1-(6,7-dihydro-5H-benzo[6,7]cyclohepta[1,2-c]pyridazin-3-yl)-N³-((7S)-7-((2-carboxyphenyl)methyl)amino-6,7,8,9-tetrahydro-5H-benzo[7]annulen-2-yl)-1H-1,2,4-triazole-3,5-diamine | =C(H)— | (2-HOOC-C₆H₄)-CH₂-NH- | B |

TABLE 1-continued

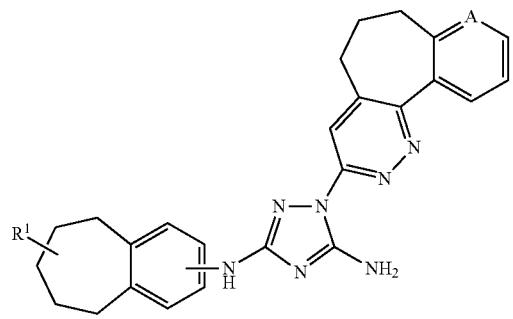
(Ia)

| Cpd # | Compound Name | A | R¹ | IC$_{50}$ |
|---|---|---|---|---|
| 30 | 1-(6,7-dihydro-5H-benzo[6,7]cyclohepta[1,2-c]pyridazin-3-yl)-N³-((7S)-7-((3-bromophenyl)methyl)amino-6,7,8,9-tetrahydro-5H-benzo[7]annulene-2-yl)-1H-1,2,4-triazole-3,5-diamine | =C(H)— | 3-bromobenzyl-NH- | B |
| 31 | 1-(6,7-dihydro-5H-benzo[6,7]cyclohepta[1,2-c]pyridazin-3-yl)-N³-((7S)-7-(dimethylamino)-6,7,8,9-tetrahydro-5H-benzo[7]annulene-2-yl)-1H-1,2,4-triazole-3,5-diamine | =C(H)— | (CH$_3$)$_2$N- | A |
| 32 | 1-(6,7-dihydro-5H-benzo[6,7]cyclohepta[1,2-c]pyridazin-3-yl)-N³-((7S)-7-(cyclobutylamino)-6,7,8,9-tetrahydro-5H-benzo[7]annulene-2-yl)-1H-1,2,4-triazole-3,5-diamine | =C(H)— | cyclobutyl-NH- | A |
| 33 | 1-(6,7-dihydro-5H-benzo[6,7]cyclohepta[1,2-c]pyridazin-3-yl)-N³-((7S)-7-(3-pentylamino)-6,7,8,9-tetrahydro-5H-benzo[7]annulene-2-yl)-1H-1,2,4-triazole-3,5-diamine | =C(H)— | 3-pentyl-NH- | A |
| 34 | 1-(6,7-dihydro-5H-benzo[6,7]cyclohepta[1,2-c]pyridazin-3-yl)-N³-((7S)-7-((2,2-dimethylpropyl)amino)-6,7,8,9-tetrahydro-5H-benzo[7]annulene-2-yl)-1H-1,2,4-triazole-3,5-diamine | =C(H)— | (CH$_3$)$_3$CCH$_2$NH- | A |
| 35 | 1-(6,7-dihydro-5H-benzo[6,7]cyclohepta[1,2-c]pyridazin-3-yl)-N³-((7S)-7-(di(cyclopentylmethyl)amino)-6,7,8,9-tetrahydro-5H-benzo[7]annulene-2-yl)-1H-1,2,4-triazole-3,5-diamine | =C(H)— | di(cyclopentylmethyl)N- | B |
| 36 | 1-(6,7-dihydro-5H-benzo[6,7]cyclohepta[1,2-c]pyridazin-3-yl)-N³-((7S)-7-((cyclopentylmethyl)amino)-6,7,8,9-tetrahydro-5H-benzo[7]annulene-2-yl)-1H-1,2,4-triazole-3,5-diamine | =C(H)— | cyclopentylmethyl-NH- | A |

TABLE 1-continued

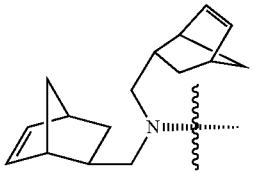

(Ia)

| Cpd # | Compound Name | A | R¹ | IC$_{50}$ |
|---|---|---|---|---|
| 37 | 1-(6,7-dihydro-5H-benzo[6,7]cyclohepta[1,2-c]pyridazin-3-yl)-N³-((7S)-7-(di(bicyclo[2.2.1]hept-2-en-5-ylmethyl)amino)-6,7,8,9-tetrahydro-5H-benzo[7]annulene-2-yl)-1H-1,2,4-triazole-3,5-diamine | =C(H)— | 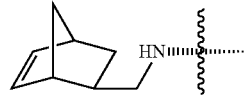 | B |
| 38 | 1-(6,7-dihydro-5H-benzo[6,7]cyclohepta[1,2-c]pyridazin-3-yl)-N³-((7S)-7-((bicyclo[2.2.1]hept-2-en-5-ylmethyl)amino)-6,7,8,9-tetrahydro-5H-benzo[7]annulene-2-yl)-1H-1,2,4-triazole-3,5-diamine | =C(H)— | 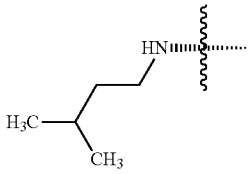 | A |
| 39 | 1-(6,7-dihydro-5H-benzo[6,7]cyclohepta[1,2-c]pyridazin-3-yl)-N³-((7S)-7-(3-methylbutylamino)-6,7,8,9-tetrahydro-5H-benzo[7]annulene-2-yl)-1H-1,2,4-triazole-3,5-diamine | =C(H)— | 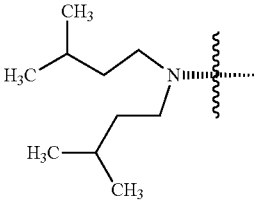 | A |
| 40 | 1-(6,7-dihydro-5H-benzo[6,7]cyclohepta[1,2-c]pyridazin-3-yl)-N³-((7S)-7-(di(3-methylbutyl)amino)-6,7,8,9-tetrahydro-5H-benzo[7]annulene-2-yl)-1H-1,2,4-triazole-3,5-diamine | =C(H)— | 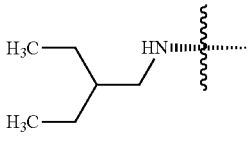 | B |
| 41 | 1-(6,7-dihydro-5H-benzo[6,7]cyclohepta[1,2-c]pyridazin-3-yl)-N³-((7S)-7-(2-ethylbutylamino)-6,7,8,9-tetrahydro-5H-benzo[7]annulene-2-yl)-1H-1,2,4-triazole-3,5-diamine | =C(H)— | 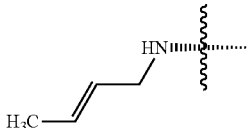 | A |
| 42 | 1-(6,7-dihydro-5H-benzo[6,7]cyclohepta[1,2-c]pyridazin-3-yl)-N³-((7S)-7-(but-2-enylamino)-6,7,8,9-tetrahydro-5H-benzo[7]annulene-2-yl)-1H-1,2,4-triazole-3,5-diamine | =C(H)— | 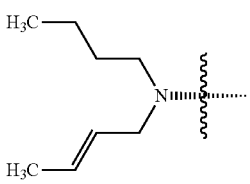 | A |
| 43 | 1-(6,7-dihydro-5H-benzo[6,7]cyclohepta[1,2-c]pyridazin-3-yl)-N³-((7S)-7-(butyl(but-2-enyl)amino)-6,7,8,9-tetrahydro-5H-benzo[7]annulene-2-yl)-1H-1,2,4-triazole-3,5-diamine | =C(H)— | | A |

TABLE 1-continued

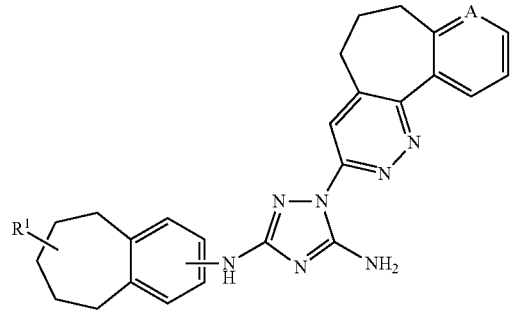

(Ia)

| Cpd # | Compound Name | A | R¹ | IC$_{50}$ |
|---|---|---|---|---|
| 44 | 1-(6,7-dihydro-5H-pyrido[2',3':6,7]cyclohepta[1,2-c]pyridazin-3-yl)-N³-((7S)-7-(t-butoxycarbonylamino)-6,7,8,9-tetrahydro-5H-benzo[7]annulene-2-yl)-1H-1,2,4-triazole-3,5-diamine | =N— | (t-Boc-NH-) | D |
| 46 | 1-(6,7-dihydro-5H-pyrido[2',3':6,7]cyclohepta[1,2-c]pyridazin-3-yl)-N³-((7S)-7-amino-6,7,8,9-tetrahydro-5H-benzo[7]annulene-2-yl)-1H-1,2,4-triazole-3,5-diamine | =N— | H$_2$N— | A |
| 47 | 1-(6,7-dihydro-5H-pyrido[2',3':6,7]cyclohepta[1,2-c]pyridazin-3-yl)-N³-((7S)-7-(dimethylamino)-6,7,8,9-tetrahydro-5H-benzo[7]annulene-2-yl)-1H-1,2,4-triazole-3,5-diamine | =N— | (CH$_3$)$_2$N— | B |
| 48 | 1-(6,7-dihydro-5H-pyrido[2',3':6,7]cyclohepta[1,2-c]pyridazin-3-yl)-N³-((7S)-7-(diethylamino)-6,7,8,9-tetrahydro-5H-benzo[7]annulene-2-yl)-1H-1,2,4-triazole-3,5-diamine | =N— | (Et)$_2$N— | A |
| 49 | 1-(6,7-dihydro-5H-pyrido[2',3':6,7]cyclohepta[1,2-c]pyridazin-3-yl)-N³-((7S)-7-(dipropylamino)-6,7,8,9-tetrahydro-5H-benzo[7]annulene-2-yl)-1H-1,2,4-triazole-3,5-diamine | =N— | (n-Pr)$_2$N— | A |
| 50 | 1-(6,7-dihydro-5H-pyrido[2',3':6,7]cyclohepta[1,2-c]pyridazin-3-yl)-N³-((7S)-7-(di(cyclopropylmethyl)amino)-6,7,8,9-tetrahydro-5H-benzo[7]annulene-2-yl)-1H-1,2,4-triazole-3,5-diamine | =N— | (cyclopropyl-CH$_2$)$_2$N— | A |
| 51 | 1-(6,7-dihydro-5H-pyrido[2',3':6,7]cyclohepta[1,2-c]pyridazin-3-yl)-N³-((7S)-7-(di(3-methylbutyl)amino)-6,7,8,9-tetrahydro-5H-benzo[7]annulene-2-yl)-1H-1,2,4-triazole-3,5-diamine | =N— | ((CH$_3$)$_2$CHCH$_2$CH$_2$)$_2$N— | B |
| 52 | 1-(6,7-dihydro-5H-pyrido[2',3':6,7]cyclohepta[1,2-c]pyridazin-3-yl)-N³-((7S)-7-(cyclobutylamino)-6,7,8,9-tetrahydro-5H-benzo[7]annulene-2-yl)-1H-1,2,4-triazole-3,5-diamine | =N— | cyclobutyl-NH— | A |

TABLE 1-continued

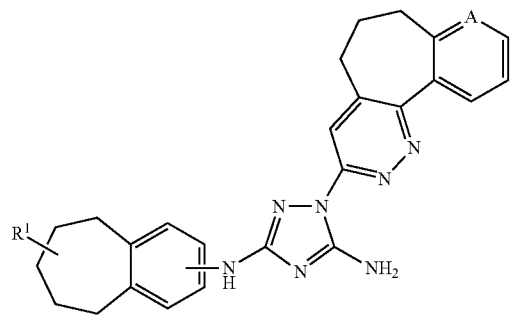

(Ia)

| Cpd # | Compound Name | A | R¹ | IC$_{50}$ |
|---|---|---|---|---|
| 53 | 1-(6,7-dihydro-5H-pyrido[2',3':6,7]cyclohepta[1,2-c]pyridazin-3-yl)-N³-((7S)-7-(cyclohexylamino)-6,7,8,9-tetrahydro-5H-benzo[7]annulene-2-yl)-1H-1,2,4-triazole-3,5-diamine | =N— | HN-cyclohexyl | A |
| 54 | 1-(6,7-dihydro-5H-pyrido[2',3':6,7]cyclohepta[1,2-c]pyridazin-3-yl)-N³-((7S)-7-(methylethyl)amino)-6,7,8,9-tetrahydro-5H-benzo[7]annulene-2-yl)-1H-1,2,4-triazole-3,5-diamine | =N— | HN-CH(CH₃)₂ | A |
| 55 | 1-(6,7-dihydro-5H-pyrido[2',3':6,7]cyclohepta[1,2-c]pyridazin-3-yl)-N³-((7S)-7-(cyclopentylamino)-6,7,8,9-tetrahydro-5H-benzo[7]annulene-2-yl)-1H-1,2,4-triazole-3,5-diamine | =N— | HN-cyclopentyl | NA |
| 56 | 1-(6,7-dihydro-5H-pyrido[2',3':6,7]cyclohepta[1,2-c]pyridazin-3-yl)-N³-((7S)-7-(2-butylamino)-6,7,8,9-tetrahydro-5H-benzo[7]annulene-2-yl)-1H-1,2,4-triazole-3,5-diamine | =N— | HN-sec-butyl | NA |

IC$_{50}$ activity:

A = <1 μM

B = 1 to 10 μM

C = >10 to 20 μM

D = >20 μM

TABLE 2

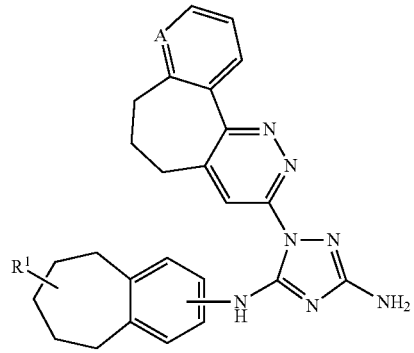

(Ib)

| Cpd # | Compound Name | A | R¹ | IC₅₀ |
|---|---|---|---|---|
| 12 | 1-(6,7-dihydro-5H-benzo[6,7]cyclohepta[1,2-c]pyridazin-3-yl)-$N^5$-(7-(pyrrolidin-1-yl)-6,7,8,9-tetrahydro-5H-benzo[7]annulene-1-yl)-1H-1,2,4-triazole-3,5-diamine | =CH— | pyrrolidin-1-yl-methyl | A |
| 14 | 1-(6,7-dihydro-5H-benzo[6,7]cyclohepta[1,2-c]pyridazin-3-yl)-$N^5$-((7S)-7-(t-butoxycarbonylamino)-6,7,8,9-tetrahydro-5H-benzo[7]annulene-2-yl)-1H-1,2,4-triazole-3,5-diamine | =CH— | t-Boc-NH— | D |

IC₅₀ activity:
A = <1 μM
B = 1 to 10 μM
C = >10 to 20 μM
D = >20 μM

TABLE 3

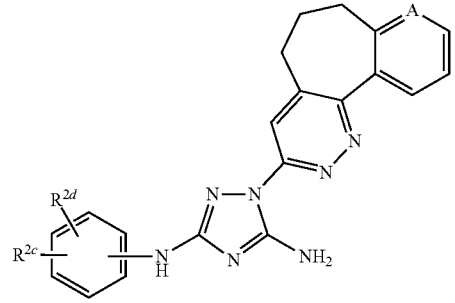

(II)

| Cpd # | Compound Name | A | $R^{2c}$ | $R^{2d}$ | IC₅₀ |
|---|---|---|---|---|---|
| 45 | 1-(6,7-dihydro-5H-pyrido[2',3':6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine | =N— | 4-(pyrrolidin-1-yl)piperidin-1-yl | —F | D |

IC₅₀ activity:
A = <1 μM
B = 1 to 10 μM
C = >10 to 20 μM
D = >20 μM

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of inhibiting Axl activity in a mammalian cell, wherein the method comprises contacting the cell with an effective amount of a compound of formula (I):

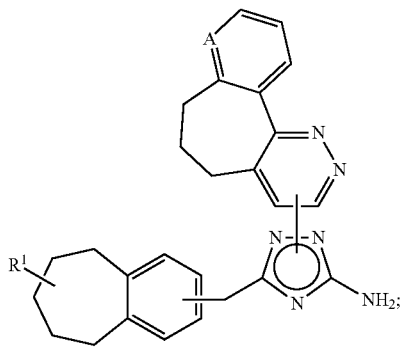

wherein:
A is =C(H)— or =N—;
R¹ is —N(R²)R³, —N(R²)C(O)R³ or —N(R²)—R⁴—C(O)OR³;
or R¹ is an N-heterocyclyl optionally substituted by one or more substituents selected from the group consisting of halo and —R⁴—C(O)OR²;
each R² and R³ is hydrogen, alkyl, alkenyl, optionally substituted aralkyl, optionally substituted cycloalkyl, optionally substituted cycloalkylalkyl and optionally substituted heteroarylalkyl; and
each R⁴ is independently selected from the group consisting of a direct bond and an optionally substituted straight or branched alkylene chain;
as an isolated stereoisomer or mixture thereof, or a pharmaceutically acceptable salt thereof;
provided that the compound of formula (I) is not a compound selected from the group consisting of:
1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N³-(7-((bicyclo[2.2.1]heptan-2-yl)amino)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N³-(7-((bicyclo[2.2.1]heptan-2-yl)(methyl)amino)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N³-((7-piperidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N³-((7-azetidin-1-yl)-6,7,8,9-tetrahydro-5H-benzo[7]annulene-2-yl)-1H-1,2,4-triazole-3,5-diamine;
1-(6,7-dihydro-5H-benzo[6,7]cyclohepta[1,2-c]pyridazin-3-yl)-N³-((7-(R)-pyrrolidin-1-yl)-6,7,8,9-tetrahydro-5H-benzo[7]annulene-2-yl)-1H-1,2,4-triazole-3,5-diamine; and
1-(6,7-dihydro-5H-benzo[6,7]cyclohepta[1,2-c]pyridazin-3-yl)-N³-(7-diethylamino-6,7,8,9-tetrahydro-5H-benzo[7]annulene-2-yl)-1H-1,2,4-triazole-3,5-diamine;
or a pharmaceutical composition comprising a pharmaceutically acceptable excipient and a therapeutically effective amount of a compound of formula (I), as an isolated stereoisomer or mixture thereof, or a pharmaceutically acceptable salt thereof;
and wherein the Axl activity in the mammalian cell is associated with a disease or condition in the mammal.

2. The method of claim 1 wherein the disease or condition is selected from rheumatoid arthritis, vascular disease, vascular injury, psoriasis, visual impairment due to macular degeneration, diabetic retinopathy, retinopathy of prematurity, kidney disease, osteoarthritis and cataracts.

3. The method of claim 1 wherein a manifestation of the disease or condition is solid tumor formation in the mammal.

4. The method of claim 1 wherein the disease or condition is selected from breast carcinoma, renal carcinoma, endometrial carcinoma, ovarian carcinoma, thyroid carcinoma, non-small cell lung carcinoma and uveal melanoma.

5. The method of claim 1 wherein a manifestation of the disease or condition is liquid tumor formation in the mammal.

6. The method of claim 5 wherein the disease or condition is myeloid leukemia or lymphoma.

7. The method of claim 1 wherein the disease or condition is endometriosis.

8. The method of claim 1 wherein the disease or condition is metastasis to the liver.

9. The method of claim 1 wherein the disease or condition is a cell proliferative disorder.

10. The method of claim 9 wherein the cell proliferative disorder is selected from renal cell carcinoma, clear cell carcinoma of kidney, renal cell adenocarcinoma, invasive ductal carcinoma, invasive lobular carcinoma, ductal carcinoma, lobular carcinoma in situ, metastatic breast cancer, basal cell carcinoma, squamous cell carcinoma, malignant melanoma, Karposi's sarcoma, small cell lung carcinoma, non-small cell lung carcinoma, bronchial adema, pleuropulmonary blastoma, malignant mesothelioma, brain stem glioma, hyptothalamic glioma, cerebellar astrocytoma, cerebral astrocytoma, medullablastoma, ependymal tumor, oligodendroglial tumor, meningioma, neuroectodermal tumor, pineal tumor, prostate cancer, testicular cancer, penile cancer, uterine cancer, cervical cancer, ovarian cancer, vaginal cancer, vulval cancer, uterine sarcoma, ovarian germ cell tumor, anal cancer, colon cancer, colorectal cancer, esophageal cancer, gallbladder cancer, stomach cancer, pancreatic cancer, pancreatic cancer-Islet cell cancer, rectal cancer, small-intestine cancer, salivary gland cancer, hepatocellular carcinoma, cholangiocarcinoma, mixed hepatocellular cholangiocarcinoma, primary liver cancer intraocular melanoma, retinoblastoma, rhabdomyosarcoma, laryngeal cancer, hypopharyngeal cancer, nasopharyngeal cancer, oropharyngeal cancer, lip cancer, oral cancer, squamous neck cancer, metastatic paranasal sinus cancer, B cell lymphoma, C cell lymphoma, non-Hodgkins lymphoma, cutaneous T cell lymphoma, Hodgkins disease, lymphoma of the central nervous system, acute myelogenous leukemia, acute lymphoblastic leukemia, chronic lymphocytic leukemia, chronic myelogenous leukemia, hairy cell leukemia, thyroid cancer, thymoma, malignant thymoma, bladder cancer, sarcoma of the soft tissue, osteosarcoma, malignant fibrous histiocytoma and lymphosarcoma.

* * * * *